(12) United States Patent
Pfeiffer et al.

(10) Patent No.: US 8,998,817 B2
(45) Date of Patent: Apr. 7, 2015

(54) BLOOD PRESSURE MEASURING DEVICE AND METHOD FOR MEASURING THE BLOOD PRESSURE OF A LIVING BEING

(75) Inventors: Ulrich Pfeiffer, Munich (DE); Tobias Thomamueller, Bruckmuehl (DE); Reinhold Knoll, Munich (DE)

(73) Assignee: UP-MED GmbH, Munich (DE)

( * ) Notice: Subject to any disclaimer, the term of this patent is extended or adjusted under 35 U.S.C. 154(b) by 511 days.

(21) Appl. No.: 12/870,434

(22) Filed: Aug. 27, 2010

(65) Prior Publication Data
US 2011/0054330 A1    Mar. 3, 2011

Related U.S. Application Data

(60) Provisional application No. 61/237,793, filed on Aug. 28, 2009.

(51) Int. Cl.
  *A61B 5/02*    (2006.01)
  *A61B 5/022*   (2006.01)

(52) U.S. Cl.
  CPC ......... *A61B 5/02233* (2013.01); *A61B 5/02225* (2013.01)

(58) Field of Classification Search
  USPC .................................. 600/480–510
  See application file for complete search history.

(56) References Cited

U.S. PATENT DOCUMENTS

| 5,255,686 | A |   | 10/1993 | Takeda et al. |         |
|-----------|---|---|---------|---------------|---------|
| 5,343,878 | A | * | 9/1994  | Scarberry et al. | 128/898 |
| 5,551,437 | A | * | 9/1996  | Lotscher      | 600/485 |
| 5,680,869 | A |   | 10/1997 | Ogura         |         |
| 6,224,558 | B1| * | 5/2001  | Clemmons      | 600/490 |
| 6,338,719 | B1|   | 1/2002  | Drzewiecki    |         |
| 2004/0249292 | A1 | * | 12/2004 | Davis et al. | 600/481 |
| 2005/0187481 | A1 |   | 8/2005  | Hatib et al. |         |
| 2006/0135872 | A1 |   | 6/2006  | Karo et al.  |         |
| 2007/0179386 | A1 |   | 8/2007  | Michard et al. |       |
| 2007/0203416 | A1 | * | 8/2007  | Lowe         | 600/485 |
| 2009/0216134 | A1 |   | 8/2009  | Hollinger et al. |     |
| 2010/0106029 | A1 |   | 4/2010  | Fraden       |         |
| 2010/0324428 | A1 |   | 12/2010 | Pfeiffer     |         |

FOREIGN PATENT DOCUMENTS

| DE | 297 19 501 U1   | 12/1997 |
| DE | 198 59 392 A1   | 7/2000  |
| DE | 202 00 048 U1   | 5/2002  |
| DE | 696 20 088 T2   | 11/2002 |
| DE | 10 2005 019755 A1 | 11/2006 |
| DE | 60 2005 003311 T2 | 9/2008  |
| EP | 1034735 A2      | 9/2000  |
| EP | 1813187 A1      | 8/2007  |

(Continued)

OTHER PUBLICATIONS

Search Report for International Application No. PCT/EP2010/005138, mailed Mar. 10, 2011.

*Primary Examiner* — Michael Kahelin
*Assistant Examiner* — Mitchell E Alter
(74) *Attorney, Agent, or Firm* — Leydig, Voit & Mayer, Ltd.

(57) ABSTRACT

A blood pressure measuring device includes a flexible element configured to at least partially surround a body part and having a stiffening element configured to stiffen the flexible element; and at least one pressure sensor element attached to the flexible element.

24 Claims, 7 Drawing Sheets

(56) References Cited

FOREIGN PATENT DOCUMENTS

| | | |
|---|---|---|
| JP | 2002-517270 A | 6/2002 |
| JP | 2007-260293 A | 10/2007 |
| JP | 08-150127 A | 7/2008 |
| JP | 10-201723 A | 9/2010 |
| JP | 2001-187029 A | 8/2014 |
| WO | WO 0195798 A2 | 12/2001 |
| WO | WO 2008121454 A1 | 10/2008 |
| WO | WO 2009100927 A1 | 8/2009 |

* cited by examiner

BLOOD PRESSURE MEASURING DEVICE AND METHOD FOR MEASURING THE BLOOD PRESSURE OF A LIVING BEING

CROSS REFERENCE TO PRIOR APPLICATIONS

Priority is claimed to U.S. Provisional Application No. 61/237,793, filed Aug. 28, 2009, the entire disclosure of which is incorporated by reference herein.

FIELD

The invention relates to a device and to a method for measuring the blood pressure of a living being. In particular, the invention relates to a device and to a method for determining parameters involving the heart-lung interaction in a living being.

BACKGROUND

In medical practice, there are many situations in which it is necessary to obtain information about the condition of the circulatory system. In particular, clinical medicine often requires certain parameters so that decisions can be made about specifically influencing the cardiovascular system, for instance, to decide whether it would be advisable to replenish the circulatory system with an infusion solution, or whether—as an alternative or to what extent—the circulatory system should be assisted by means of circulation-active drugs. The parameters of the heart-lung interaction (HLI) have proven to be especially useful in this context. These parameters, however, are usually based on an invasive measurement of the arterial blood pressure and require laborious cannulization of an arterial vessel.

Non-invasive methods for measuring HLI parameters have not been very satisfactory so far because of their poorer signal quality. The pulsatile signals, that is to say, the pressure changes in the arterial vessels caused by the pulse, are measured directly over the tissue using an external device. In this process, damping effects, caused by damping in the tissue and in the measuring device, have a considerable negative impact on the signal-to-noise ratio. This is why non-invasive methods fail in actual practice, U.S. patent application 2005/187481 A1 puts forward methods for determining HLI parameters. Mention is made of a non-invasive measurement employing finger clips, arm cuffs or ear clips. However, it is not disclosed how a suitable signal quality can be achieved with these measuring instruments.

U.S. Pat. No. 5,255,686 discloses a device for non-invasive, continuous blood-pressure measurement. The measuring component is a conventional blood-pressure cuff with which the systolic, diastolic and mean blood pressures are determined.

SUMMARY OF THE INVENTION

An aspect of the present invention is to put forward a device and a method for measuring blood pressure which, in comparison to the prior art, improve the signal quality during a non-invasive measurement of pulsatile signals.

In an embodiment a means of a blood pressure measuring device (20) is provided comprising a flexible element (30) that is configured to at least partially surround a body part (10), whereby at least one pressure sensor element (40) is attached to the flexible element (30), and the flexible element (30) has a stiffening means (31) with which the flexible element (30) can be stiffened.

Blood pressure measuring devices are devices with which pulsatile signals, that is to say, pressure oscillations in blood-carrying vessels of a living being, preferably a human being, can be measured. It is intended for non-invasive use.

A cuff is preferably used as the flexible element, preferably a cuff that can be wrapped around the body part, or a closed tubular cuff. Preferably, the flexible element has a compression element with which the flexible element can be adapted to the surface profile of a three-dimensional object, preferably to the surface profile of a body part of a living being, especially preferably to the surface profile of a body part of a human being. The profile of at least one boundary surface of the adapted flexible element then corresponds essentially to the inverse contour of the surface profile to which the flexible element has been adapted. The flexible element is preferably deformable. Preferably, the flexible element is elastically or plastically deformable. Especially preferably, the flexible element can be bent and/or compressed and/or twisted. The deformation of the flexible element makes it possible to provide at least one surface of the flexible element with any desired surface profile by superimposing locally concave and/or convex profile structures. The deformation of the flexible element is preferably passive, that is to say, it is brought about by one or more forces acting upon the flexible element. This deformation is preferably generated by pressing the flexible element onto the surface profile. This pressing is preferably done manually or by a pressure means, especially preferably by a pneumatic pressure means. Preferably, the flexible element surrounds the body part partially, especially preferably, the flexible element surrounds the body part completely. For instance, the flexible element can be placed over the entire surface around the thigh or calf, around the wrist, a finger or the upper arm of a person, so that it adapts to the surface in question, partially or completely covering or surrounding said body part. The dimensions of the flexible element are preferably adapted to the specific body part for which the blood pressure measuring device is intended. Preferably, the flexible element has the shape of a closed cylindrical jacket. Especially preferably, the flexible element has the shape of a mat, preferably with a rectangular mat surface that can be shaped into a cylindrical jacket.

A pressure sensor element is attached to the flexible element. It can detect pressures and pressure fluctuations, and can convert them into electric signals. These signals are transmitted by means of a sensor cable or preferably wirelessly for further processing.

The attachment of the pressure sensor element is preferably such that the pressure sensor element is in contact with one of the surfaces of the flexible element. Preferably, the pressure sensor element is affixed to one of the surfaces of the flexible element. Especially preferably, the pressure sensor element is incorporated into one of the surfaces of the flexible element. The preferred surface for the attachment is the inside of the flexible element. In this context, the inside is the side facing the body part. Preferably, the attached pressure sensor element can be removed and re-attached. For this purpose, the pressure sensor element preferably has a connection element such as a Velcro closure, a suction cup, adhesive surfaces or snaps. This connection element is preferably arranged between the flexible element and the pressure sensor element. Especially preferably, the connection element is located on the surface of the pressure sensor element facing away from the body surface. In the preferred attachment of the pressure sensor element on the inside of the flexible element, it is in direct contact with the body part in question. When the flexible element is pressed onto the body part, the pressure sensor element is pressed against the body part, as a result of which the signal-to-noise ratio during the acquisition of the measured values is improved.

The blood pressure measuring device preferably has several pressure sensor elements. Preferably, the pressure sensor elements are on one or more axes at known distances with respect to each other. Thus, for instance, the pulse wave velocity in an artery can be measured if at least two pressure sensor elements are attached to the inside of the flexible element in such a way that they are on an axis that runs essentially parallel to an artery of the body part, and if the distance from one pressure sensor element to the next pressure sensor element is known in each case.

The flexible element has a stiffening means. It is configured to stiffen the flexible element in such a way that it is no longer deformable. Preferably, the stiffening means is configured to stiffen the flexible element in such a way that it is no longer elastically or plastically deformable. Especially preferably, the stiffening means is configured to stiffen the flexible element in such a way that it can no longer be bent and/or compressed and/or twisted. As a result of being stiffened by the stiffening means, the flexible element preferably becomes incompressible. Preferably, the shape of the flexible element is not substantially changed when it is stiffened by the stiffening means, so that the surface profile of the flexible element is essentially retained. Preferably, the surface profile of the flexible element that has been adapted to the body part of a living being, preferably a human being, is retained when it is stiffened. Preferably, the stiffening means is present essentially in the entire spatial extension of the flexible element. Preferably, the stiffening means is essentially uniformly integrated into the flexible element, so that the stiffening means stiffens the flexible element essentially uniformly.

For instance, just several layers of sheets made of paper or of a similar material can constitute a stiffening means. Already starting at approximately 20 sheets stacked on top of each other and having a paper weight of 80 $g/m^2$, the sheets can be stiffened by rolling up the stack. The stack can no longer be compressed. This effect can be observed, for example, in a cylinder consisting of several sheets of paper. When such a stack is employed as the stiffening means, the stack especially preferably contains 50±10 sheets of paper (preferably 80 $g/m^2$). For instance, such a stack of paper is wrapped around an extremity, as a result of which the stack becomes stiff.

The stiffening means can preferably be activated via a control line, as a result of which the flexible element is stiffened. Preferably, the stiffening means can be deactivated again via a control line, as a result of which the flexible element once again becomes deformable.

The blood pressure measuring device according to the invention essentially prevents damping of the pulsatile signals by components of the device and/or by air outside of the device. This translates into a high signal quality. This is made possible by the hydraulically optimized contacting of the pressure sensor element with the body part that is relevant for the measurement.

The contact of the pressure sensor element with the body part is improved by the hydraulically optimized contacting of the surface profile of the flexible element that has been adapted to the body part.

In another embodiment of the present invention, a blood pressure measuring device is provided in which the pressure sensor element (40) is a pressure sensor (41) embedded in a gel cushion (44).

A gel cushion preferably consists of a sealed pouch whose cavity contains a filling. The filling is preferably a fluid having a viscosity between 0.1 mPa·s and $10^7$ mPa·s, especially preferably between 0.6 mPa·s and $10^6$ mPa·s. Especially preferably, the fluid is a silicon gel.

The gel cushion can preferably be adapted to the surface profile of a body part. This adaption is preferably done by simply pressing the gel cushion against the surface of the body part. The profile of the boundary surface of the adapted flexible element then essentially matches the inverse contour of the surface profile to which the flexible element has been adapted. The adaptation is possible because the gel cushion is deformable. Preferably, the gel cushion is elastically deformable. Especially preferably, the gel cushion can be bent and/or compressed and/or twisted.

The pressure sensor is a sensor that converts pressure oscillations in the gel cushion into electric signals. The pressure sensor is preferably located directly in the fluid. Preferably, the pressure sensor is located in the center of the gel cushion.

Since a pressure sensor is inserted into a cushion filled with gel or another liquid, an optimized contact can be achieved between the pressure sensor element and the body part. Preferably, the gel cushion is positioned on the body part over a large surface area by means of contact, preferably by means of skin contact. As a result, pressure fluctuations stemming from a blood vessel of the body part with which the gel cushion is in contact are transferred to the gel cushion in essentially undamped form. Then, owing to the fluid in the cushion, the pressure fluctuations can propagate unimpeded and can be measured by the sensor. Since the gel cushion is a pressure sensor element that is attached to the flexible element, the pressure fluctuations are no longer transferred to other components, provided that the flexible element has been stiffened. Therefore, the energy of the pressure waves does not reach adjacent components of the blood pressure measuring device or the air, as a result of which the energy is essentially completely available for the measurement.

In this context, preferably more signal energy is transferred from the body part to the pressure sensor element. This improves the signal-to-noise ratio. The larger the surface area of contact with the body part, the larger the surface area of transfer and thus also the higher the signal energy that is available for the measurement.

In another embodiment of the present invention, a blood pressure measuring device is put forward in which other sensors are additionally provided, particularly a sensor device for measuring the impedance and/or electrodes.

These additional sensors are preferably provided at one or more places of the blood pressure measuring device, as desired, especially preferably on the inside of the flexible element. Very especially preferably, the sensors are attached directly to a gel cushion in which a pressure sensor is embedded.

The sensors are preferably electrodes for measuring impedance and/or potential, and/or they are photoelectric detection elements or excitation elements and/or capacitively measuring sensors, and/or acceleration sensors, and/or strip electrodes. They are preferably configured to measure other biosignals.

Thus, for instance, the pulsatile blood flow can generally be measured via the resistance, preferably via the alternating-current resistance of the body part section, when at least two electrodes are employed, whereby one of them is employed (at least temporarily) as an excitation electrode, while the other one is employed (likewise at least temporarily) as a detection electrode.

For example, in order to measure the impedance, four electrodes or strip electrodes (e.g. a metal strip or a strip made of a flexible conductive material) are attached in a circle to the inside of the flexible element, in other words, in such a way that the electrodes surround the body part when the blood pressure measuring device has been placed onto a body part. In this context, the outer two electrodes are preferably provided to inject a current, preferably an alternating current of up to 100 mA. The inner electrodes are then provided for the high-ohmic measurement of the impedance signal. Since the volume of the detected body part section changes due to the pulsatile inflow of blood, which is an electric conductor, it is possible to acquire a signal that runs synchronously to the pulsatile arterial blood flow in the detected body section, if blood flow is present. Pulsatile signals can be measured if a pressure below the diastolic blood pressure is applied onto the body part from the outside (for instance, by means of a blood-pressure cuff). Intermittent pulsatile signals which, however, drop down again to zero, are measured employing a pressure exerted from the outside that is between the diastolic and the systolic blood pressure.

When electrodes are used, conductive gel that reduces the transfer resistance to the body part is preferably provided between an electrode and the body part. A sensor cable, or especially preferably a wireless unit, is provided for purposes of transmitting the sensor signals. When a sensor fulfills the function of measuring the pressure, it can preferably also replace a pressure sensor element.

In another embodiment of the present invention, a blood pressure measuring device is put forward in which an external fixation means (50) is provided that is or can be arranged at least partially around the flexible element (30).

The external fixation means is preferably a pressure means or a compression means. Especially preferably, a pulling means is provided as the external fixation means. For example, the external fixation means is a belt system having one or more belt buckles or Velcro closures, preferably a system consisting of one or more latching strips or, especially preferably, locking buckles (of the type used, for example, in ski boots). Especially preferably, the external fixation means is an elastic element that can preferably be filled, preferably quickly filled, with a material, preferably a fluid or gas, preferably via at least one connecting tube, and that can be evacuated, so that its volume can preferably be changed. Especially preferably, such an elastic element is a conventional blood-pressure cuff. Likewise especially preferably, the external fixation means is a combination of various of the above-mentioned embodiments. Preferably, the external fixation means can be wrapped around, especially preferably like a cuff or stocking. Preferably, the external fixation means has the shape of a closed cylindrical jacket. Especially preferably, the elastic element has the shape of a mat, preferably with a rectangular mat surface that can assume the shape of a cylindrical jacket.

Preferably, the external fixation means is provided on the outside of the flexible element. Preferably, the external fixation means is connected, at least temporarily, to the flexible element at one or more points. This connection is preferably in the form of one or a combination of the following connection possibilities: adhesion, sewing, vulcanization, one or more snaps, one of more Velcro closures. Especially preferably, the external fixation means can be connected to the flexible element by means of a force exerted by the external fixation means. The external fixation means is preferably arranged on the flexible element so as to overlap at one or preferably several of the boundary edges of the flexible element, especially preferably, it is arranged at one or more of the boundary edges of the flexible element so as to be flush with the flexible element and to cover it. Preferably, the external fixation means is arranged on the flexible element so as to cover it only partially.

Preferably, the external fixation means and the flexible element are realized in one single unit. This can preferably be configured so that it can be re-used. The external fixation means preferably has the capacity to exert a force, and thus pressure, onto the flexible element, which preferably presses the flexible element against the body part. Preferably, this force affixes the flexible element onto the body part. Preferably, the force acts upon the outside of the flexible element, that is to say, upon the surface of the flexible element facing away from the body part. Preferably, the orientation of the force exerted by the external fixation means is perpendicular to surface, preferably perpendicular to the outside of the flexible element, and it acts in the direction of the body part. Preferably, the external fixation means exerts a surface force that preferably acts perpendicularly upon every point of the surface of the flexible element, preferably perpendicularly upon every point on the outside of the flexible element. Preferably, the external fixation means presses the flexible element against the body part, preferably in such a manner that the flexible element is affixed to the body particularly by the pressure, especially preferably so that the inside of the non-stiffened flexible element facing the body part is adapted to the surface profile of the body part. Especially preferably, the external fixation means presses the non-stiffened flexible element against the body part in such a manner that essentially no air pockets remain between the flexible element and the body part, especially preferably, so that essentially no air pockets remain between one or more of the pressure sensor elements attached to the inside of the flexible element. Preferably, the pressure sensor element or the attached pressure sensor elements, as well as preferably additional sensors, are pressed—together with the flexible element—against the body part by the force of the external fixation means.

Preferably, the degree of fixation, that is to say, the force with which the fixation means presses the flexible element against the body part, can be controlled or can be regulated automatically. Preferably, a control line is provided for control purposes. In a preferred embodiment of the external fixation means as an elastic element, or especially preferably as a blood-pressure cuff, this control line is preferably a tube that feeds air or a fluid into the preferably elastic element or into the especially preferred blood-pressure cuff, preferably by means of a pump. As a general substitute for the pump, preferably a pressure tank can also be provided that has a sufficient capacity and that is preferably replenished with pressure, either externally or by an internal pump, during phases when it is not performing a measurement.

In order to determine the measured value of the degree of fixation required for the regulation, preferably a pressure sensor element is provided that preferably measures the contact pressure between the flexible element and the body part. Especially preferably, this pressure sensor element is one of or a group of several of the pressure sensor elements already provided for the measurement of the pulsatile signals.

In another embodiment of the present invention, a blood pressure measuring device (20) is provided in which the pressure sensor element (40) is a sensor or a combination of sensors from the set of the following sensors: electrodes (42) for impedance and/or potential measurement, photoelectric sensors, capacitive sensors, acceleration sensors.

The combination of the sensors preferably has different, especially preferably only identical, sensors. A pressure sensor element preferably has any desired number of these sensors.

In another embodiment of the present invention, a blood pressure measuring device (20) is provided in which the stiffening means (31) has at least one air-tight pouch (32) having at least one connection tube (36).

The air-tight pouch preferably consists of a material characterized by flexibility, preferably by a high degree of air-impermeability. It preferably encloses a cavity. The air-tight pouch is preferably shaped like a pipe or like a tube. Especially preferably, the air-tight pouch is mat-like, preferably with a rectangular mat surface. Especially preferably, the air-tight pouch has approximately the shape of a toroidal surface. This is preferably a flat torus. The air-tight pouch can preferably be deformed together with the flexible element. Preferably, one or more of the air-tight pouches is/are located inside the flexible element. If there are several air-tight pouches, they are preferably arranged in a uniform distribution.

Likewise preferably, the air-tight pouch consists of two layers of a material that is very stiff and elongation-resistant (for example, rubberized fabric or a material similar to a car tire or to a bicycle tire) that are connected to each other so as to be air-tight (for instance, welded or vulcanized). The connection delimits at least one air-tight, preferably elongated, chamber. In this embodiment, the thickness of the flexible element is preferably not greater than that of the two connected layers of material. The layers are preferably pre-oriented with respect to each other so that, when the at least one chamber is filled with compressed air, the flexible element is shaped in a way that is adapted to the body part (e.g. the arm).

The connection tube is preferably provided in order to pump air or a special gas or a fluid into the air-tight pouch and to evacuate it.

The cavity preferably diminishes in size or disappears completely when the pouch is evacuated. When an elastic element that can be filled with gas is employed as the external fixation means, and particularly when a conventional blood-pressure cuff is employed as the external fixation means, the control line of the external fixation means, which in this case is a tube, and the connection tube of the air-tight pouch are preferably connected to each other in such a way—or especially preferably configured so that they can be connected to each other—that air or the special gas can be exchanged between the external fixation means and the air-tight pouch. Then, the venting of the flexible element preferably brings about the inflation of the external fixation means and/or vice-versa. Preferably, at least two such connection tubes are provided, so that, in each case, at least one tube is available for inflating the air-tight pouch and one tube for venting the air-tight pouch. This reduces the time needed for the air exchange.

A connection tube preferably has at least one valve by means of which material flows can preferably be restricted in any desired direction, or especially preferably completely blocked.

In another embodiment of the present invention, a blood pressure measuring device (20) is provided in which the air-tight pouch (32) has essentially incompressible elements whose volume in a vacuum changes by less than 50% in comparison to the volume at atmospheric pressure.

The volume of these elements preferably changes by less than 25%, especially preferably by less than 10%, particularly preferably by less than 1%. Ideally, the change in the volume in a vacuum as compared to the volume at atmospheric pressure approaches zero.

Preferably, a plurality of these essentially incompressible elements fill the air-tight pouch. The shape of these elements is preferably conical, angular or a mixture of both. Many elements suitable for this purpose are conceivable. These elements are preferably very small (e.g. in the order of magnitude of constituents of a powder all the way to the size of chestnuts) and they can preferably be arranged with each other in any desired way. When the agglomerate made up of these elements is compressed, these elements preferably become tangled, wedged together or compressed, and the arrangement of the elements solidifies, so to speak.

The essentially incompressible elements are, for instance, plastic granules, rice, particles made of polystyrene or a similar plastic, shredded paper, paper pellets, sheets of paper, styrofoam beads, sawdust, salt, any powder or similar elements. The essentially incompressible elements located in the air-tight pouch are preferably a mixture of different types of incompressible elements. As the incompressible elements, special preference is given to sheets of paper or of another material that are layered to form a stack like the stack of paper described above as the implementation of a stiffening means. The difference is only that the above-mentioned stack of paper is now located in the air-tight pouch.

Another example of a possibility is a magnetorheological fluid having a suitable composition as the filling of the air-tight pouch. The incompressible elements here are small, magnetically polarizable particles (e.g. iron powder) that float in a suspension. Magnetorheological fluids are known from the state of the art. In this case, it is preferably sufficient if the described air-tight pouch is not necessarily air-tight, but rather only fluid-tight with respect to the magnetorheological fluid. In this case, the connection tube is preferably not present, either. The application of a magnetic field (for example, by switching on an electromagnetic array that acts upon the surface of the stiffening means, or else by wrapping the flexible element or the blood pressure measuring device with at least one electromagnetic and/or permanent-magnetic assembly that is configured, for example, in the form of a mat, or even by just using one single magnet and/or electromagnet) makes it possible to achieve a preferably abrupt stiffening of the stiffening means. The fluid essentially retains the shape it had acquired before. When the magnetic field is switched off or removed, an equally fast disappearance of the stiffening occurs.

In another embodiment of the present invention, a blood pressure measuring device (20) is provided in which the air-tight pouch (32) has entangled fibers.

The fibers are preferably thin, preferably crimped filaments of preferably any desired material.

The entanglement of the fibers preferably consists of a randomly crossed arrangement of the fibers, which preferably become tangled with each other. Especially preferably, the entanglement is brought about by drops of adhesive on the intersections of the fibers. Entangled fibers can be, for example, fabrics, thin-layered cotton, fine layers of crepe paper, non-woven paper and the like.

Preferably, the entangled fibers form a nonwoven material in which the other elements present in the air-tight pouch preferably mix with each other. This mixture preferably fills up the cavity of the air-tight pouch. The entangled fibers preferably form at least one layer inside the air-tight pouch. Preferably, the essentially incompressible elements are also arranged in at least one layer in the air-tight pouch.

In another embodiment of the present invention, a blood pressure measuring device (20) is provided in which the air-tight pouch (32) has styrofoam beads (33) and entangled fibers (34).

The styrofoam beads preferably consist of a material having a high surface friction coefficient, especially styrofoam. They have a radius R. This radius varies or preferably lies between 0.01 mm and 10 mm, especially preferably between 0.15 mm and 4 mm.

Preferably, the air-tight pouch has entangled fibers.

When the air-tight pouch is evacuated, the styrofoam beads preferably come to lie close to each other and are wedged together as a result of friction. The wedged-together agglomerate of styrofoam beads and entangled fibers is preferably stiff, thereby stiffening the flexible element.

Particularly preferred is a flexible element that has a stiffening means, an air-tight pouch filled with styrofoam beads and preferably entangled fibers. This implements the principle of a vacuum splint or a vacuum mattress.

In another embodiment, the stiffening means (31) comprises a stack of sheets made of paper (311) or of another similar material.

This stack of paper layers is preferably located in the air-tight pouch. Since the layers lie on top of each other with virtually no space between them (for instance, they are stacked as described above), even without any evacuation, the air-tight pouch is already very pressure-resistant and provides good properties for measuring the blood pressure. If the air-tight pouch is then additionally evacuated, the layers of paper form a firm agglomerate whose stiffness increases further. (FIG. 3: Sample 3). This accounts for a very favorable signal-to-noise ratio.

In another embodiment of the present invention, a blood pressure measuring device (20) is provided in which the flexible element (30) has at least one latching strip (51).

The latching strip preferably has a sawtooth surface profile on at least one side. This sawtooth profile is preferably configured in such a way that, when two latching strips are placed over each other in opposite directions, they become wedged together when they are moved in a direction that is crosswise to the sawtooth profile until they can no longer be moved due to the wedging. Preferably, however, they do not become wedged together when they are moved in the opposite direction.

Preferably, the blood pressure measuring device has an inner and an outer latching strip. This is a kind of the external fixation means that can be provided in addition to or instead of an existing external fixation means. The inner latching strip is preferably attached to the inside of the flexible element, so that the surface with the sawtooth profile faces the body part. The outer latching strip is attached to the side of flexible element facing away from the body, preferably to the external fixation means, so that its sawtooth profile preferably faces away from the body. The inner latching strip preferably has an eyelet onto which preferably a strap can be secured and can be passed through a tab preferably attached to the outer latching strip. In this manner, after the flexible element has been placed around a body part, the two latching strips can be affixed with respect to each other by pulling on the strap. Especially preferably, the inner latching strip can be passed directly through the tab on the outer latching strip. Thus, by pulling on the end of the inner latching strip, the latching strips can affixed with respect to each other. Owing to the preferred combination of the strap and the latching strips, the flexible element can be pressed against the body part. The latching strips function as an external fixation means. The latching strips are preferably immovable with respect to each other after the flexible element has been stiffened. The latching strips can preferably be provided as a substitute for the conventional blood-pressure cuff if the objective is to dispense with the latter.

In another embodiment of the present invention, a blood pressure measuring device (20) is put forward in which a control device (60) for controlling the stiffening means (31) is provided.

The control device preferably comprises a pump and preferably additional elements such as, for example, an electronic processor unit and/or controllable valves for purposes of controlling the stiffening means manually or electronically. The control device is preferably connected to the additional elements and/or to the components of the blood pressure measuring device via the existing control lines. Preferably, the control device is accommodated in a housing that is preferably attached to the flexible element, especially preferably to the external fixation means. Preferably, the control device is configured to regulate the stiffening means in order to attain defined target values such as, for instance, the level of the vacuum. Especially preferably, the control device is configured to use a regulation unit to regulate the external fixation means or preferably the blood-pressure cuff in order to attain defined target values such as, for example, the degree of the fixation.

In another embodiment of the present invention, a blood pressure measuring device (20) is put forward in which an analysis device is provided in order to analyze and/or display and/or store measured data.

The analysis device can preferably be accommodated together with the control device in a housing. It preferably has a processor unit that is preferably intended to analyze measured data in terms of parameters that are relevant for the measurement such as the pulse contour parameters, namely, stroke volume, maximum rate of pressure rise, and especially the HLI parameters (pulse pressure variation—PVV, stroke volume variation SVV). Especially preferably, the processor unit of the control device is accessed for this purpose, so that it is not necessary to provide the analysis device with its own processor unit. Preferably, a display such as, for instance, a compact LCD or OLED, is provided. It preferably allows a visual display of preferably calculated parameters, especially preferably of state variables, very especially preferably of measured values. Moreover, the data can preferably be stored and the course of the measurement can preferably be recorded in the analysis device. The analysis device is preferably provided in such way that measurement-relevant information can later be read out on a computer.

In an embodiment, a means of a method according to the invention is provided for measuring the blood pressure of a living being, and comprising the following steps:

placing a flexible element (30) having a pressure sensor element (40) onto a body part (10) that is relevant for the measurement, so that the flexible element (30) assumes a shape that is adapted to the body part;

stiffening the flexible element (30) in the shape that is adapted to the body part;

measuring the pressure signal over a certain period of time during which the flexible element (30) is in the stiffened state;

returning the flexible element (30) back to the flexible state.

This method makes it possible to determine the pulse contour parameters and the dynamic parameters of the heart-lung interaction (HLI) such as, for example, PPV, SVV, PEPV as well as other derived variables based on the heart-lung interaction without the need for laborious cannulization of an arterial vessel. As a result, these parameters can be determined non-invasively. With a corresponding evaluation of the pulsatile signals, it can be assumed that the pulsatile signals measured in this precise manner correspond directly to the arterial pressure. For this evaluation, preferably the systolic and diastolic blood pressures are measured at least once by means of an oscillometric or auscultatory method, and the systolic and diastolic values of the measured pulsatile signals are calibrated to the previously determined values.

Preferably, this method is employed in a patient who is being ventilated, especially in a patient who is under controlled ventilation. In such patients under controlled ventilation, these parameters can provide crucial information since here, volume changes can be brought about by the pressure exerted on the lungs and indirectly on the vessels as well as on the heart of the patient.

The flexible element is preferably put in place by manually pressing the flexible element onto the body part. Owing to the deformability of the flexible element, it can already be brought into the desired shape ahead of time and especially preferably, the flexible element is configured so as to be already pre-shaped. When the flexible element is put in place, it adapts to the body part in such a way that the surface of the flexible element acquires an inverse contour of the surface profile of the body part. Preferably, no air gaps are left between the body part and the surface of the flexible element facing the body part. Preferably, the flexible element is placed in such a way that the pressure sensor element comes to lie over an artery running through the body part. For instance, when the *Arteria brachialis* of the upper arm is measured, the pressure sensor element would preferably be positioned on the inside of the upper arm. The flexible element is placed in such a way that it preferably covers the body part at least partially. Especially preferably, the flexible element covers the entire available surface area of the body part. Preferably, the flexible element surrounds the body part. Preferably, the flexible element is pulled over the body part. Especially preferably, the flexible element is wrapped around the body part. When the flexible element is placed onto the body, preferably the pressure with which the flexible element makes contact with the body is measured by a pressure sensor element so that information is available about the degree of the fixation. Especially preferably, the pressure sensor element used for this purpose is a pressure sensor element that has already been attached to the flexible element. Preferably, the pressure resulting from the placement does not exceed 10% of the diastolic blood pressure.

The flexible element is preferably placed onto a body part of a living being, preferably a human being. Preferably the upper arm, especially preferably the wrist, of a person is suitable for measuring the blood pressure. In other living beings, equivalent body parts, or especially the tail, are suitable for this purposes.

The stiffening is carried out by activating the stiffening means. As a result of the stiffening of the flexible element, it is no longer deformable and it solidifies in the shape adapted to the body part. Preferably, the flexible element is no longer plastically or elastically deformable as a result of the stiffening. Especially preferably, the flexible element becomes incompressible as a result of the stiffening. Particularly preferably, the flexible element can no longer be twisted or bent as a result of the stiffening. Due to the stiffening of the flexible element, the pressure sensor elements attached to the flexible element are rigidly brought into contact with the body part. Due to the stiffening, at least one of the sensors attached to the blood pressure measuring device is brought into a hydraulically optimized contact with the body part.

The measurement of the pulsatile signals takes place over the course of time. The pressure fluctuations caused by the pulse are transferred to the pressure sensor elements attached to the flexible element, where they can be picked up. These signals are strongly damped in comparison to the blood-pressure signals picked up during an invasive measurement of the arterial blood pressure since they are measured indirectly over the tissue and the pressure sensor element. These signals are thus preferably picked up indirectly from the outside. This is preferably done over the course of time, so that a series of measured values are present at specific points in time. In the stiffened state of the flexible element, the contacting of the pressure sensor element is hydraulically more advantageous than in the flexible state, which is why the measurement is preferably carried out when the flexible element is in its stiffened state.

The pressure signal is preferably measured over a certain period of time. The measurement time here preferably encompasses at least one respiratory cycle or breathing cycle, preferably several, especially preferably three or more respiratory cycles. This can be achieved, for example, in that the pressure that is exerted by the external fixation means—preferably by the stiffened flexible element—onto the body part is maintained over a prolonged period of time within the pulsatile range or is released at a slow rate. In contrast to the oscillometric blood-pressure measurement—in which essentially the mean pressure in the cuff is decisive at the point in time of the beginning of the pulsatility, at the point in time of the maximum fluctuations or at the point in time of the disappearance of the pulsatility—in case of the HLI method according to the present invention, the arterial pulsations are preferably calibrated on the basis of previously known systolic and diastolic values and are themselves then evaluated with a precise form analysis.

In this context, the breathing cycle is preferably determined on the basis of the pulsatile fluctuations over the course of time. As an alternative, the identification of a breathing cycle can also be made by means of other measuring methods, for instance, on the basis of the thoracic electric impedance signal, which can be detected through EKG electrodes. Other preferred methods for determining the breathing cycle are described, for example, in European patent specification EP 01 813 187. Here, other advantageous evaluation possibilities for the blood-pressure data acquired according to the invention are described, to which reference is hereby made. For instance, it is preferably possible to suppress the display of certain parameters if, for example, arrhythmia or irregular breathing (in other words, not controlled ventilation) is present.

Since the flexible element can be returned from the stiffened state back to the flexible state, the flexible element and also the entire blood pressure measuring device can advantageously be re-used.

In another method according to the invention, an external fixation means (50) is attached over the flexible element (30). Preferably, this is done after the flexible element has been put in place. The attachment is preferably done in such a manner that the external fixation means preferably exerts a force onto the flexible element, preferably uniformly along the contact surface of the body part and of the flexible element, so that the flexible element is pressed against the body part and preferably the flexible element is affixed to the body part. The pressure sensor elements or other sensors attached to the flexible element are pressed against the body part by the external fixation means. Thus, the flexible element and the pressure sensor elements attached to the inside of the flexible element facing the body part are hydraulically brought into contact with the body part. Preferably, the external fixation means is configured in such a way that a pre-determined degree of fixation is achieved.

The degree of fixation is related to the force that the external fixation means exerts on the flexible element. It can be varied by adjusting the external fixation means. Thus, it can be ensured that the flexible element is held in place securely but not too tightly. When the external fixation means is being adjusted, the pressure with which the flexible element is brought into contact with the body part is preferably measured by a pressure sensor element so that information about the degree of fixation is available. Especially preferably, the pressure sensor element employed for this purpose is a pressure sensor element that has already been attached to the flexible element.

The fixation is preferably done by means of a belt system. Here, at least one belt is wrapped around the flexible element and the body part, and it is preferably pulled and affixed by means of a buckle. The belt can also be affixed by a combination of an eyelet arranged on the belt and a Velcro closure. Preferably, the belt is permanently joined to the flexible element on one side.

Especially preferably, the fixation is done by means of at least one latching strip. Especially preferably, the fixation is done by means of an inner and an outer latching strip, which are attached suitably for the device. In this case, the flexible element is placed onto the body part in such a way that the inner latching strip comes to lie on the outer latching strip. The latching strips can be moved with respect to each other, thus reinforcing the fixation of the flexible element. Movement in the opposite direction causes the latching strips to become wedged together, so that this movement is only possible over the length of one sawtooth at the maximum. The sawtooth profile of the latching strips prevents the fixation means from automatically loosening. The latching strips are preferably moved by pulling on a strap that connects the two ends of the latching strips to each other. Preferably, the flexible element is first closed loosely using the strap. Pulling on the strap to affix the flexible element can preferably be done automatically, for instance, by means of bellows powered by compressed air. Especially preferably, it is also possible to dispense with the strap, and the inner latching strip can be passed directly through the tab of the outer latching strip. Then, it is possible to move the latching strips with respect to each other by pulling on the end of the inner latching strip that has already been passed through the tab.

Especially preferably, the external fixation means is in the form of an elastic element that is filled with liquid or gas. The elastic element is affixed tightly to the flexible element. Preferably, it is already affixed to the outside of the flexible element. The flexible element and the pressure sensor element are pressed tightly against the body part when the elastic element is filled with liquid or gas. The elastic element expands as a result of being filled and thus presses the flexible element as well as attached pressure sensor elements against the body part. The elastic element is preferably filled via one or more connection tubes.

In another preferred method, the flexible element (30) is stiffened so as to become incompressible.

The incompressible stiffening makes it impossible to further compress the flexible element, preferably in the areas where a pressure sensor element has been attached to the flexible element. Especially preferably, the flexible element cannot be compressed in a circular area around the body part—for instance, an extremity—that is surrounded by the blood pressure measuring device. As a result, pressure oscillation that act upon the flexible element cannot be transferred to the material of the flexible element. A pressure oscillation acting upon the incompressible stiffened element does not cause a deformation of the flexible element, and thus does not damp the pressure oscillation due to energy absorption in the flexible element due to deformation.

In another preferred method, the flexible element (30) is stiffened by evacuating the air contained in it.

The stiffening means is preferably activated by pumping out or evacuating the air in the stiffening means, provided that the stiffening means has an air-tight pouch. Preferably, it is also possible to create a vacuum. For this purpose, the air inside the air-tight pouch is extracted via at least one connection tube. Air is continuously extracted from the air-tight pouch until a vacuum is created inside the air-tight pouch. The extraction is preferably carried out by means of a pump connected to the end of the connection tube. The air-tight pouch is located inside the flexible element, so that the stiffening means is generally activated by evacuating the air that is present inside the flexible element.

In another preferred method, the flexible element (30) is stiffened by being filled with compressed air.

Preferably, when two layers of a material that is that is very stiff and elongation-resistant (for example, rubberized fabric or a material similar to a car tire or to a bicycle tire) is used as the air-tight pouch, the flexible element is stiffened by being filled with compressed air. Due to the fact that the material is very stiff and elongation-resistant, the pouch hardens immediately. In order to obtain optimal measured results, a pressure value should be selected that is close to the mean arterial pressure. For this purpose, at least one chamber of the air-tight pouch is inflated. The requisite pressure for hardening the flexible element exceeds the systolic pressure to such an extent that, as a result, the systolic pressure cannot deform the air-tight pouch, and consequently, no interferences or damping can occur. By further inflating the air-tight pouch with a high pressure, the inner layer of the air-tight pouch can expand slightly, thus increasing the pressure being exerted onto the arm of the patient. In this manner, the regulation can be oriented towards the mean arterial pressure (measuring pressure).

In another preferred method, a conventional blood-pressure cuff is employed as the external fixation means (50).

A conventional blood-pressure cuff is well-known from the state of the art. It can be placed onto a body part, preferably onto the upper arm or the wrist, whereby the placement preferably involves wrapping the cuff around or pulling the cuff over the body part. It is then affixed on the body part in this position by means of attached Velcro and/or belt closures. When the cuff is filled with air or with a liquid, its volume increases and it presses against the body part. The pressure can be lowered by releasing filling material. Thus, it is preferably also possible to set not the volume, but rather the pressure in the cuff in such a way that a compression of the body part in question causes the pressure sensor element attached to the flexible element to be indirectly associated with the volume fluctuations of the arterial blood vessels.

Such a blood-pressure cuff is preferably placed around the flexible element, especially preferably, it is pulled over the flexible element. It then covers the flexible element at least partially. When a conventional blood-pressure cuff is filled, it exerts pressure on the flexible element that, together with the pressure sensor elements attached to it, is then pressed against the body part and compresses the body part.

In another preferred method, the evacuated air is pumped into the external blood-pressure cuff when the flexible element (30) is being stiffened.

Preferably, there is at least one connection tube with preferably at least one valve between the conventional blood-pressure cuff and the flexible element. Especially preferably, a pump is provided in addition to the connection tube between the flexible element and the conventional blood-pressure cuff. Air from the flexible element can then be pumped into the blood-pressure cuff. In this manner, the flexible element is emptied and thus stiffens, while at the same time, the blood-pressure cuff is filled with air and presses the flexible element against the body part.

This preferred method entails two advantages. First of all, just one actuator, preferably the pump, is sufficient to control the flexible element as well as the external fixation means, preferably the conventional blood-pressure cuff. Secondly, the flexible element is pumped out at the same time as the blood-pressure cuff is being pumped up, so that all in all, the time needed for these two methods is kept to a minimum.

In another preferred method, the systolic, diastolic and mean blood pressures are measured by varying the pressure in the blood-pressure cuff.

The pressure that the blood-pressure cuff exerts on the flexible element can then—as would be the case if the flexible element were not present—be utilized to measure the systolic, diastolic and mean blood pressures by means of the known oscillatory measuring principle. For this purpose, air or a liquid is pumped into or discharged from a conventional blood-pressure cuff. Preferably, the flexible element is not in its stiffened state during this process. The pulsatile signals are preferably measured by means of one of the pressure sensor elements attached to the flexible element. Especially preferably, the measurement is carried out at intervals that each consist of the variation of the degree of the fixation of the external fixation means, preferably of the variation of the pressure in the conventional blood-pressure cuff, with a subsequent stiffening of the flexible element, followed by the measurement of pulsatile signals by one of the pressure sensor elements with a final return of the flexible element back to its flexible state.

The oscillometric blood-pressure measurement according to the state of the art is fundamentally based on the fact that, with a blood-pressure cuff that is placed on the outside, the arterial blood vessels exhibit caliber fluctuations as long as the cuff pressure is less than the systolic blood pressure and greater than the diastolic blood pressure. These caliber fluctuations in the arterial blood vessels, in turn, cause pulsatile pressure fluctuations in the blood-pressure cuff. In the case of a cuff pressure that is greater than the systolic blood pressure, the arterial blood vessels are completely compressed during the entire cardiac cycle, and consequently, no fluctuations occur in the caliber of the vessels and no pulsatile pressure fluctuations occur in the cuff. If the cuff pressure falls below the diastolic blood pressure, then the arterial blood vessels are completely open during the entire cardiac cycle, and likewise, no pulsatile fluctuations occur. The actual measuring principle of the scillometric blood-pressure measurement is that the pressure in the cuff is continuously increased until no more pulsatile pressure fluctuations occur. Then the pressure is reduced, usually continuously, and the pressure values in the cuff are determined at which the pulsatility begins, reaches it maximum and disappears. On the basis of these characteristic values, the systolic blood pressure, the mean blood pressure and the diastolic blood pressure are then ascertained.

In another preferred method, the flexible element (30) is stiffened at an arterial pressure between the mean blood pressure and the diastolic blood pressure.

Preferably, the pressure of the external fixation means is set in such a way that the external fixation means exerts a pressure between the systolic pressure and the diastolic pressure in the pulsatile range, preferably a pressure in the pulsatile range at which the largest arterial oscillations occur. In this range, the amplitude of the pulsatile signals is at its highest and is thus easiest to detect.

For this purpose, the pressure of the external fixation means on the flexible element and thus on the body part can preferably be increased starting from zero until the first pulsatile signals can be detected—this prevailing pressure then corresponds roughly to the diastolic pressure. If the pressure is then further increased, a second point in time is reached when it is no longer possible to measure any pulsatile signals—this corresponds to the systolic pressure. These values can also be ascertained in the opposite direction, that is to say, coming from an elevated pressure, it is possible to ascertain when a first pulsatile signal is received (systolic pressure), and from what point onwards no signal is received any more (diastolic pressure) as the pressure is further reduced. If a value is employed between these two pressures that are being applied at these points in time, then this is in the pulsatile range. The closer to the center of this range the measurement is carried out—thus preferably in the mean value between the two pressures, i.e. the mean pressure—the greater the amplitudes are. Especially preferably, the measurement is carried out just below the mean pressure. Very especially preferably, the pressure at which the measurement is carried out, ($P_{meas}$) is estimated on the basis of the formula:

$$P_{meas}=P_{sys}+\tfrac{1}{2}(P_{sys}-P_{dias})$$

wherein $P_{sys}$ stands for the systolic blood pressure and $P_{dias}$ stands for the diastolic blood pressure. Ideally, however, $P_{meas}$ is ascertained by means of integration over time after the calibration of the pulsatile signal.

It is in this range that the maximum amplitudes of the pulsatile signals can be expected, and thus the signals that are best for evaluation purposes.

Experience has shown that the largest amplitudes of the pulsatile signals can be expected at a pressure in a conventional cuff between the mean blood pressure and the diastolic blood pressure. In particular, experience has shown that the largest amplitudes occur just below the mean blood pressure. Due to the stiffening of the flexible element in this pressure range, the pressure sensor elements attached to the flexible element are brought into a hydraulically optimized contact in a range that is optimal for the measurement of the pulsatile signals. Preferably, the pulsatile signals are measured over time with a flexible element that has been stiffened in this pressure range.

In another preferred method, the stiffening of the flexible element (30) is controlled and/or the degree of the fixation (50) is controlled by a control device (60) and/or the sensor values are acquired, especially also analyzed and/or displayed and/or stored.

Preferably, it is possible to keep the stiffening of the flexible element constant, preferably through regulation by the control unit. When a stiffening means is employed that is activated by creating a vacuum, the stiffening can preferably be regulated in terms of the level of the vacuum. Especially preferably, the stiffening of the flexible element can be systematically varied and it is possible to alternate continuously between the stiffened state and the flexible state. This preferably makes it possible to perform measurement procedures. The control is preferably carried out by means of the control unit and can, in turn, once again also be regulated in terms of specific measured values, for instance, the level of the vacuum.

Preferably, the degree of the fixation of the external fixation means can be kept constant, preferably through regulation by the control unit. The degree of the fixation is a function of the pressure that the external fixation means exerts onto the body part via the flexible element. Consequently, the degree of the fixation is preferably derived from this pressure, which is preferably measured by a pressure sensor element. Especially preferably, this pressure sensor element is a pressure sensor element that has already been attached to the flexible element. Therefore, the degree of the fixation is preferably regulated in terms of the pressure exerted onto the body part. Especially preferably, the degree of the fixation can be systematically varied. This preferably makes it possible to perform measurement procedures. The degree of the fixation is preferably controlled by the control unit. Preferably, the degree of the fixation can also be regulated in terms of certain measured values, for instance, the pressure exerted onto the body part.

The above-mentioned control and regulation procedures can be carried out independently of each other, preferably in a structured dependence with respect to each other. They preferably take place at certain points in time of the method, especially preferably during the entire method.

The analysis is preferably carried out continuously with incoming new measured data, especially preferably at one or more points in time. The analysis of the measured pulsatile signals preferably compiles the individual measured values into measured values that are associated with a heart beat. Moreover, an association can also be made with a respiratory cycle. For instance, after the removal of artifacts, it is possible to ascertain the minimum and maximum of the individual blood-pressure fluctuations per heart beat as well as the fluctuations within at least one breathing cycle (respiratory cycle).

In this manner, the desired parameters of the heart-lung interaction (HLI) can be ascertained.

With the non-invasive measurement of the HLI, it is preferably provided according to the invention that the systolic and diastolic blood-pressure values are determined in advance as boundary values, and moreover, the same applies to the variation of these values that are based on the respiratory HLI parameters.

Preferably, the HLI parameters encompass the stroke volume variation (SVV), the pulse pressure variation (PVV) and/or the pre-ejection-phase variation (PEPV). Other derived variables based on the HLI can also be calculated as HLI parameters such as, for example, the respiratory fluctuations of the pulse wave velocity or the respiratory variation range of the rate of pressure rise.

Preferably, the respiratory variation range of the HLI is ascertained. In this context, preferably the maxima and the subsequent minima are determined; alternatively the minima and the subsequent maxima, that is to say, the blood-pressure amplitude, are determined on the basis of the systolic pressure and the preceding diastolic pressure. Subsequently, the amplitude variation over the respiratory cycle is ascertained as a measure of the pulse pressure variation. Fundamentally, the pressure fluctuations that are caused by the pulsatile caliber fluctuations of the blood vessels and that are measured at a non-invasive pressure sensor element are considerably smaller than the pulsatile pressure fluctuations in the arterial blood vessel. HLI parameters such as the PPV and the SVV, however, are relative measures (as a rule they are indicated in %), and the relative percentage variation of the signal propagated into the cuff is closely associated with the respiratory variation of the HLI in the arterial blood vessel. The same applies to the PEPV which, however, is the variation range of a time-related dimension. In this configuration of the HLI measuring method, in order for the delay time between the electric activity and the mechanical ejection phase of the heart to be determined, it is possible to additionally use an electrocardiogram in order to detect the time of the beginning of the electric cardiac activity. As an alternative, the PEPV as an HLI parameter can also be acquired on the basis of the time difference between an electrocardiographic signal and a photoplethysmographic signal. Preferably, it is also possible to multiply the pulsatile signals by a factor or to employ a correction function in order to compensate for the damping of the arterial pressure signals that occurs. This factor can preferably be determined empirically by means of a statistical survey in a large patient pool. Especially preferably, the factor of the damping can then be calculated back from a direct invasive and simultaneously non-invasive measurement of the pulsatile signals and from the evaluation of these signals. This factor can then be utilized in the subsequent non-invasive measurements for purposes of converting the measured pulsatile signals into the actual and current arterial values.

The damping that occurs between the arterial "true pressure signal" and the pressure signal that occurs at the pressure sensor element is essentially a function of the compressibility of the tissue. This transfer function can be compensated for by a factor in very simplified form. Fundamentally, this is a transfer function that can be depicted, for example, by an equivalent circuit diagram that consists of series of parallel connections of resistors and capacitors and, in the simplest version of the parallel connection, that consists of a resistor and a capacitor. The numerical compensation of this transfer function is a deconvolution. If the basic characteristic of the arterial pressure curve is known (for instance, on the basis of an idealized model curve) and if the basic characteristic of the transfer function is known (for example, a resistor and a capacitor in a parallel connection), the parameters for the transfer function for the exact correction and back calculation to the "true intravasal pressure signal" can preferably be ascertained as follows: in a first step, a conventional oscillometric pressure measurement serves to ascertain the systolic and diastolic or mean arterial pressures. The flexible element here is preferably in its flexible state. In a second step, the mean pressure in the cuff is "clamped" at the pressure at which the maximum pulsatile signal quality is observed (as a rule, at the mean arterial pressure $P_{meas}=P_{sys}+\frac{1}{3}(P_{sys}-P_{dias})$ or in the $P_{meas}$ obtained through time integration). The flexible element is then stiffened in order to ensure a high signal quality.

In this manner, it is possible to employ the measured pulsatile signals in order to carry out pulse contour methods to estimate the cardiac output (CO) or the pulse contour stroke volume.

Preferably, measured values and analyzed parameters are displayed. These can preferably be displayed on a monitor and/or they can be printed out on a connected computer, especially preferably on a display device attached to the blood pressure measuring device, for instance, an LCD. The measured values and analyzed parameters can be continuously displayed, starting at the moment when they become available, but preferably they are only displayed at a certain point in time, especially preferably at several points in time.

Preferably, the data that was acquired by the method and that is necessary for subsequent processing, analysis or activation is stored. Towards this end, the control unit preferably has at least one memory element that can be read, for instance, by a connected computer. This data is stored continuously, starting at the moment when it becomes available, but preferably, it is only displayed at a certain point in time, especially preferably at several points in time.

In another preferred method, the electric impedance of the body part (10) is additionally measured.

Preferably, in addition to the measurements according to the invention, the electric impedance of the body part is measured. Especially preferably, however, it is also possible to exclusively carry out an impedance measurement of the body part. In this process, at least one excitation electrode and at least one detection electrode are used. Preferably, several excitation electrodes and detection electrodes can be employed in order to measure the electric impedance at various places of the body part. The electrodes are attached to the blood pressure measuring device. Preferably, they are attached to the flexible element so that they make contact with the skin of the body part. This contact can preferably be improved by means of a conductive gel. Owing to the resistance of the skin, subcutaneous tissue, muscle, fat, bone, blood, etc., the excitation electrodes and detection electrodes form a closed circuit through which a defined current flows that is harmless for the body, preferably an alternating current. The ohmic resistance or the alternating-current resistance brought about by the body part, preferably the extremity cylinder, can be calculated by means of the preferably separately measured voltage drop between the excitation electrode and the detection electrode or between the injection electrodes. This ohmic resistance varies with the arterial pulsations and correlates with the arterial blood flow in the body part since the vein cross sections that influence the resistance and the volume of blood in the veins change with the pulsations. In particular, the impedance or its first derivation correlates with the pulsatile change in the cross section of the arteries located, for example, in the upper arm, especially the *Arteria brachilais*. Therefore, the measurement of the impedance of the body part provides additional information about the pulsatile signals. This information is preferably combined with the measured data of the pressure sensor elements in order to yield a more exact calculation of the HLI parameters. Especially preferably, the information stemming from the impedance measurement can be utilized to correctively change the measured data from the pressure sensor elements attached to the flexible element and/or vice versa. The impedance is preferably measured continuously, especially preferably at one or more points in time, particularly preferably alternating with the measurement of the pulsatile signals by a pressure sensor element.

In another preferred method, during a measurement and/or subsequent to it, the arterial curve shape is determined on the basis of one or more of the measured pressure patterns. In this context, conventional signal transformations are preferably employed.

Preferably, values are derived from the pulsatile signals in order to carry out a pulse contour method. The absolute blood-pressure values are needed in order to carry out a pulse contour method. Since the signal quality is better than in the case of the cuffs used for the oscillometric blood-pressure measurement as known from the state of the art, a type of non-invasive continuous blood-pressure measurement is possible, including all of the further analysis possibilities such as, for instance, pulse contour methods.

In another preferred method, the stiffening of the flexible element (30) is reversed after a specific period of time.

This specific period of time is primarily a function of the type and objective of the measurement as well as of period of time during which the flexible element may be stiffened without harming the body part. Preferably, the flexible element is stiffened for a duration of at least n respiratory cycles and subsequently, the stiffening is reversed, whereby n is an element of the real numbers, preferably n=1, preferably n=2, especially preferably n=3 or more. The stiffening is reversed by deactivating the stiffening means so that the flexible element becomes deformable once again. Preferably, the flexible element becomes plastically or elastically deformable once again. When an air-tight pouch is employed as the stiffening means, said stiffening means is deactivated by feeding air into the air-tight pouch, thus inflating the air-tight pouch. This inflating procedure is done via one or more connection tubes. A pump, especially preferably a pressure tank containing sufficient compressed air, is connected to this connection tube so that the air-tight pouch can be quickly inflated.

In another preferred method, the external fixation means (50) is loosened after a specific period of time.

This specific period of time is primarily a function of the type and objective of the measurement as well as of the period of time during which the external fixation means may exert pressure onto the flexible element and thus onto the body part without harming the body part. If the external fixation means is used for too long a time, fluid is forced out of the body tissue. Preferably, the external fixation means exerts pressure for a duration of at least k respiratory cycles, after which it is loosened, whereby k is an element of the real numbers, preferably k=1, preferably k=2, especially preferably k=3 or more.

The external fixation means is loosened by loosening the straps if such are present, by loosening belt systems that might be present, and by emptying the elastic element, preferably by emptying the conventional blood-pressure cuff, in each case if such a type of fixation means is present.

BRIEF DESCRIPTION OF THE DRAWINGS

The invention will be illustrated in greater detail below on the basis of drawings. These show the following.

DETAILED DESCRIPTION

Figure 1A:
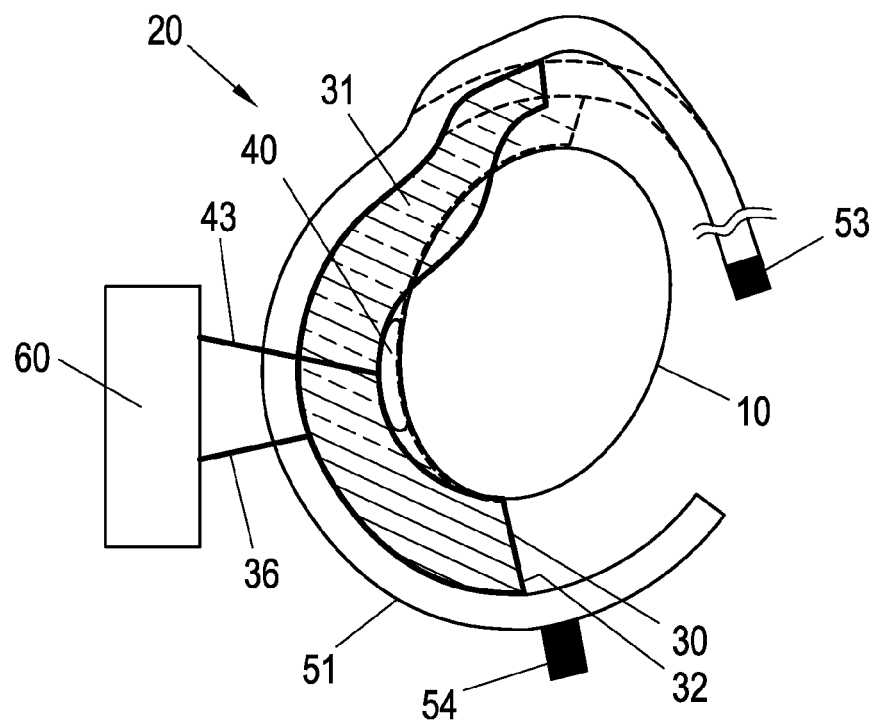
FIG. 1*a* a schematic cross section of a blood pressure measuring device according to the invention.

FIG. 1a shows a schematic cross section of a blood pressure measuring device 20 according to the invention. It comprises a flexible element 30 with a stiffening means 31 and a control line 36, a pressure sensor element 40 with a sensor cable 43, a latching strip 51, an eyelet 53, a tab 54 and a control device 60.

A body part 10 is depicted as an ellipse. The flexible element 30 is delimited by an air-tight pouch 32 that is indicated by a thick black contour. It contains a filling material consisting of styrofoam beads and entangled fibers. This filling material is indicated by cross-cross-hatching (from the top left to the bottom right), it is uniformly distributed in the air-tight pouch 32, and it serves as the stiffening means 31. The deformability is shown by way of an example in that the areas that have been changed after being adapted to the body part 10 are shown with dashed lines. A connection tube 36 is attached to the air-tight pouch 32 or to the flexible element 30 as a control line for the flexible element 30. It is drawn as a thick line. The pressure sensor element 40 is attached to the flexible element. It is attached to the surface of the flexible element 30 that faces the body part 10, in other words, to the inside. A sensor cable 43 is attached to the pressure sensor element. It is drawn as a thick line. The latching strip 51 is arranged around the flexible element 30. In the cross section shown, the latching strip 51 overlaps the flexible element 30 on two sides. The cross section shows a variant for attaching the latching strip to the flexible element 30. The latching strip has an eyelet 53 and a tab 54. These are depicted as small black squares. The sensor cable 43 of the pressure sensor element and the connection tube 36 for the flexible element 36 lead to a control device 60. This control device is depicted as a large rectangle.

When the flexible element 30 is placed onto the body part 10, it assumes a shape that is adapted to the surface of the body part when it is placed on the inside of the body part 10 and pressed against the body part 10. As a result, the inside of the flexible element 30 acquires a surface profile that is preferably in direct contact with every point of the surface of the body part 10—except for the surfaces covered by a pressure sensor element. Therefore, the pressure sensor element 40 is in direct contact with the body part 10. Once the flexible element 30 is in the shape that has been adapted to the body part, it is stiffened. For this purpose, air is extracted out of the flexible element 30, which here has an air-tight pouch 32, via the connection tube 36, and the filling of the air-tight pouch 32 is compressed. In this process, the agglomerate of styrofoam beads and entangled fibers is wedged together in such a way that its shape can no longer be changed. Thus, the shape of the flexible element can no longer be changed. This effect is reversed in that air is fed into the air-tight pouch 32 (deactivation of the stiffening means).

The ends of the latching strips 51 are moved with respect to each other by means of a strap that joins the eyelet 53 to the tab 54, so that the flexible element 30 comes to lie more tightly against the body part 10, thus pressing onto the body part 10. It is also possible to work without a strap if one end of the latching strip (the one with the eyelet 53, which however, is not necessary) is passed directly through the tab 54 and the ends of the latching strip are moved with respect to each other by pulling on this end of the strap. The pressure on the body part 10 is regulated by tightening or loosening the latching strips.

The pressure sensor element 40 is also pressed against the body part 10 by the flexible element 30 and this results in direct contact of the pressure sensor element 40 with the body part 10. Consequently, pulsatile signals of the blood vessels present in the body part can be measured. The pressure sensor element 40 converts these signals into electric signals. The electric signals are then relayed via a sensor cable 43.

The control unit 60 regulates the stiffening of the flexible element 30 and detects the measured values of the pressure sensor element 40. On the basis of the available sensor values, the control device 60 calculates characteristic values such as, for example, HLI parameters, particularly the CO, SVV, PPV, PEPV. These available sensor values and/or the calculated characteristic values are displayed by the control unit, for instance, on an LCD (not shown here) and/or they are stored. The control unit also provides all of the data so that it can be read out by a computer that can be connected via a cable or wirelessly.

The depicted device makes it possible to measure pulsatile signals with a signal-to-noise ratio that is higher than that of the state of the art. On the basis of these qualitatively better signals, informative characteristic values can be calculated. The higher signal-to-noise ratio is made possible by the optimized hydraulic contact of one or more pressure sensor elements 40 with a body part 10. The hydraulic contact is based on the possibility of stiffening a flexible element 30 using a stiffening means 31. This flexible element is first adapted to the body part 10 and then stiffened. The adaptation to the body part 10 is assisted by the pressure of the latching strip 51, so that the pressure sensor element 40 is pressed onto the body part. Once air has been evacuated out of the air-tight pouch 32, and thus the flexible element 30 has been stiffened, pulsatile signals are no longer damped due to absorption in flexible elements, and so these pulsatile signals are available for the pressure measurement in essentially undamped form.

Figure 1B:
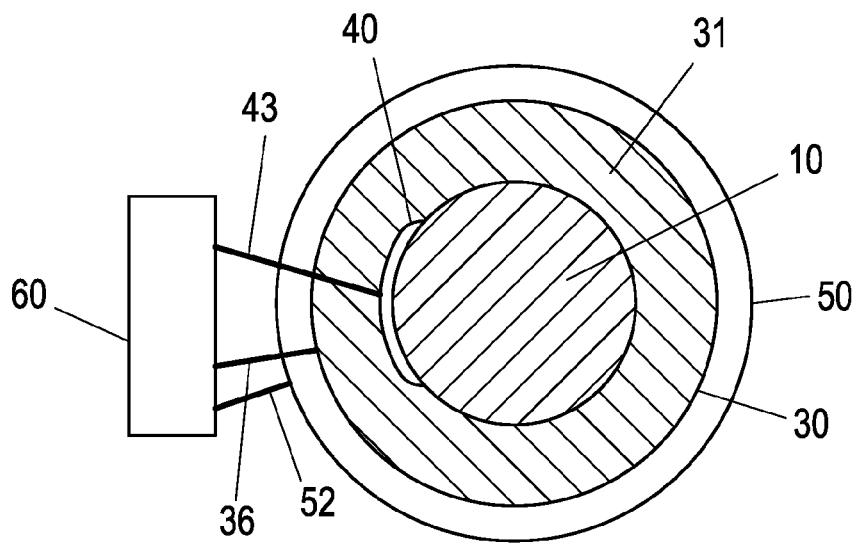
FIG. 1*b* a schematic cross section of a blood pressure measuring device according to the invention in a ring-shaped embodiment and with a blood-pressure cuff as the external fixation means.

FIG. 1b shows a schematic cross section of a blood pressure measuring device according to the invention in a ring-shaped embodiment and with a blood-pressure cuff as the external fixation means.

The body part 10 is indicated by cross-cross-hatching (from the top left to the bottom right). This is, for instance, the upper arm of a human being. The flexible element 30 is ring-shaped and has an air-tight pouch. The pouch is uniformly filled with styrofoam beads and entangled fibers. This filling, which can be stiffened, is shown in abstract form as cross-hatching (from the top left to the bottom right) and constitutes the stiffening means 31 of the flexible element 30. A pressure sensor element 40 is attached on the side of the flexible element facing the body part 10. This schematic cross section shows the attachment of the pressure sensor element 40 to the flexible element, as a result of which the pressure sensor element is flush with one of the surfaces of the flexible element. A blood-pressure cuff that serves as an external fixation means 50 is shown here in a ring-shaped version. Since the blood-pressure cuff is attached to the outside, its diameter is greater than that of the flexible element 30. The blood-pressure cuff has a connection tube 52 as a control line through which air or a fluid is filled into and let out of the cuff. The other components in the drawing correspond to those of FIG. 1*a*.

The attachment of the flexible element 31 and of the blood-pressure cuff is done by pulling it over the body part 10. The extent of the external fixation, that is to say, the pressure that the blood-pressure cuff 50 exerts onto the body part 10, can be adjusted by means of the control line 52. A gas or liquid is filled into the elastic element (the pressure exerted onto the body part is increased), or else it is let out of the elastic element (the pressure exerted onto the body part is decreased).

The advantage of the ring-shaped embodiment is that the blood pressure measuring device can be quickly placed onto the body part. However, this restricts its use to body parts that allow the flexible element 30 to be pulled over them. Moreover, the diameter of the hollow cylinder formed by the flexible element 30 has to be roughly adapted to the body part. The use of the blood-pressure cuff allows a variation of the pressure onto the body part so that it is easy to measure the blood pressure.

Figure 2:
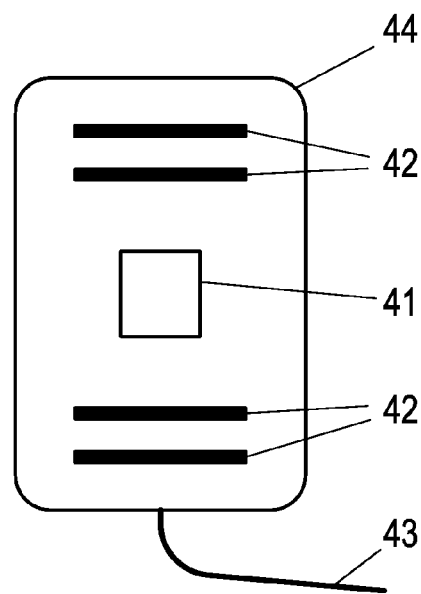
FIG. 2 a top view of a pressure sensor element that is configured as a gel cushion, whereby the impedance electrodes come to lie crosswise to the longitudinal direction of the extremity.

FIG. 2 is a top view of a pressure sensor element that is configured as a gel cushion.

The gel cushion 44 is shown as a rounded-off square. The gel cushion is filled with a fluid. The top view shows the special case of a transparent gel cushion that is filled with transparent fluid. In this manner, elements inside the gel cushion are visible in the top view.

The pressure sensor 41 embedded in the gel cushion 44 is drawn as a square in the center of the gel cushion. The pressure sensor is located in the center of the gel cushion.

This top view also shows other sensors 42. They are drawn in abstract form as dark bars. These additional sensors are electrodes for measuring the impedance. In this context, at least one electrode is provided as an excitation electrode and at least one electrode is provided as a detection electrode.

The electric signals generated by the pressure sensor 41 and by the additional sensors 42 are relayed via the sensor cable 43.

The gel cushion 44 with the integrated sensors 41, 42 constitutes a pressure sensor element that is preferably attached to the inside of flexible element 30. For this reason, it is pressed onto the body part 10 when the flexible element 30 is put in place. The contact created in this process establishes a hydraulic contact between the pressure sensor located in the gel cushion 44 and the body tissue. Pressure oscillations in a blood vessel present in the body part 10 are thus transmitted to the pressure sensor 41 via the fluid contained in the gel cushion 44. The contact surface area of the gel cushion 44 on the body part 10, which is larger than the surface area of the pressure sensor 41, means that the amplitudes of the oscillations measured on the pressure sensor 41 are higher than in the case when the pressure sensor 41 is placed directly onto the body part.

The additional sensors 42 attached to the gel cushion 44 are configured for an impedance measurement. Thus, even pulsatile signals can be measured through the skin resistance since the skin resistance changes as the vein cross section of the blood vessels changes due to the pulse. This is likewise preferably measured on the gel cushion 44 since, on the one hand, the direct pressure measurement by means of the pressure sensor 41 and the impedance measurement on the basis of the local correspondence can be better correlated with each other and, on the other hand, the gel cushion 44 ensures good contact with the body part.

Therefore, the configuration of a pressure sensor element as a gel cushion fitted with a sensor offers many measuring variants in conjunction with good contact with the body part.

Figure 3A:
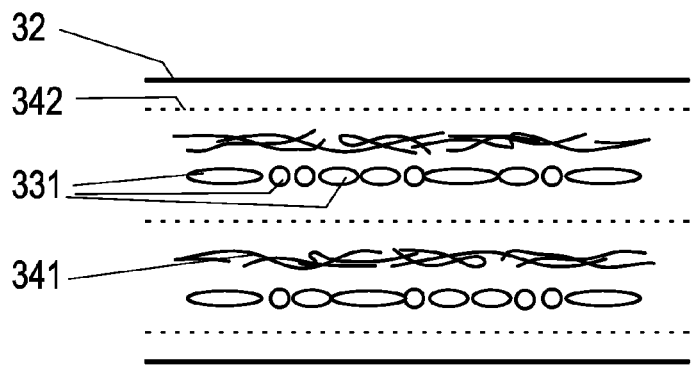
FIG. 3*a* a diagram of a preferred embodiment of the stiffening means of the flexible element in the form of an air-tight pouch filled with grains of rice and fabric as well as wool fibers.

FIG. 3*a* shows a diagram of a preferred embodiment of the stiffening means of the flexible element in the form of an air-tight pouch filled with grains of rice and fabric as well as wool fibers.

A section of the air-tight pouch 32 is indicated by a thick black boundary line at the top and at the bottom. In this embodiment, elements made of non-compressible material, in other words, essentially incompressible elements 331, are contained in the filling of the air-tight pouch 32. These elements are drawn as circles or ellipses. These are grains of rice. A thin dotted line indicates a fabric 342 as another component of the filling material. Wool fibers 341 are drawn as black, curved short lines that are entangled with each other. They are also part of the filling.

In this embodiment, the filling has a layered structure. The grains of rice 331 are embedded in layers of wool fibers 341 and fabric 342. The compressible parts of filling are compressed when the air contained in the air-tight pouch 32 is evacuated. The grains of rice are not compressed, but rather, they press against each other and become wedged together in the adjacent layers. In this manner, the air-tight pouch 32 can no longer be compressed.

Consequently, a high final solidity can be achieved by evacuating the air-tight pouch. The higher the final solidity, the more favorable the signal-to-noise ratio.

Figure 3B:
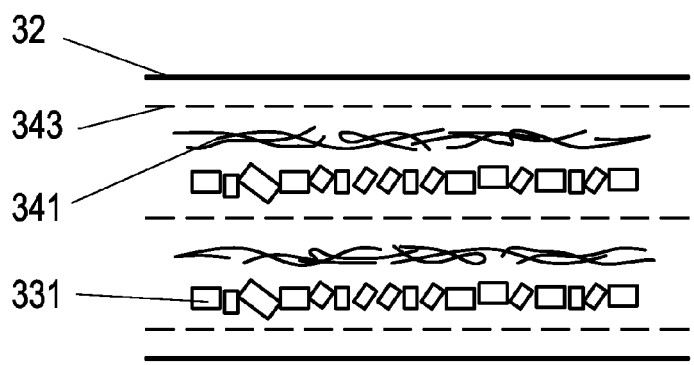
FIG. 3*b* a diagram of a preferred embodiment of the stiffening means of the flexible element in the form of an air-tight pouch filled with plastic granules, plastic nets and cotton fibers.

FIG. 3*b* shows a diagram of a preferred embodiment of the stiffening means of the flexible element in the form of an air-tight pouch filled with plastic granules, plastic nets and cotton fibers.

The difference from the previous figure is that the filling material now consists essentially of incompressible plastic granules 331, plastic nets 343 as well as cotton fibers 341. Moreover, the fillers are layered in a different sequence.

The use of plastic granules is an inexpensive option for the filling. Furthermore, during production, the size of the plastic granules can be coordinated with the dimensions of the body part to which the device is to be adapted.

Figure 3C:
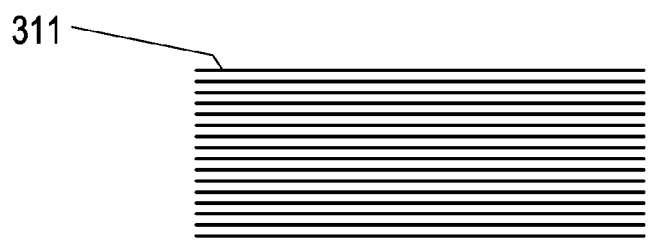
FIG. 3*c* a diagram of a preferred embodiment of the stiffening means of the flexible element in the form of a stack of paper.

FIG. 3*c* shows a diagram of a preferred embodiment of the stiffening means of the flexible element in the form of a stack of paper.

This figure shows a stack of paper consisting of several sheets 311 laid on top of each other.

When this stack is not rolled up, it is flexible. However, if it is placed inside a conventional blood-pressure cuff and wrapped around, for instance, the upper arm together with the blood-pressure cuff, then the stack of paper has a stiffening effect. It can no longer be compressed by the pulse fluctuations of the arm. In practical terms, this is a blood-pressure cuff fitted with several layers of paper on the inside. A pressure element located between the arm and the stack of paper can then measure signals having an excellent signal quality. The stack of paper can also be protected in a pouch.

In another embodiment, the air-tight pouch can also be filled with several layers of paper or a similar material. Since the layers of paper come to lie on top of each other with virtually no space between them, the pouch is already very pressure-resistant without any evacuation and has good properties for a measurement of the blood pressure. If the air-tight pouch is additionally evacuated, the layers of paper form a firm agglomerate whose stiffness is further increased.

Figure 3D:
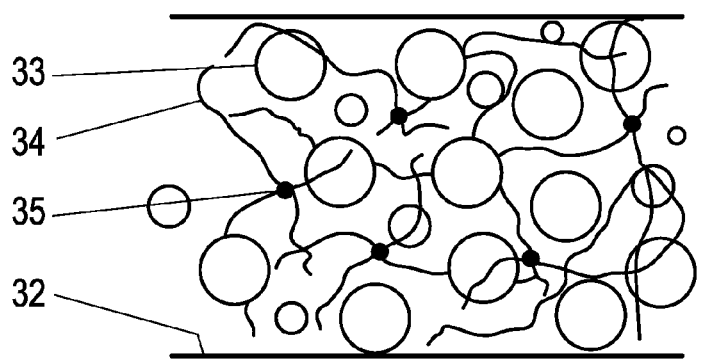
FIG. 3*d* a diagram of a preferred embodiment of the stiffening means of the flexible element in the form of an air-tight pouch filled with styrofoam beads and fibers.

FIG. 3*d* shows a diagram of a preferred embodiment of the stiffening means of the flexible element in the form of an air-tight pouch filled with styrofoam beads and fibers.

A section of the air-tight pouch 32 is indicated by a thick black boundary line at the top and at the bottom.

The styrofoam beads 33 are drawn as circles with black edges. They have different radii.

The fibers 34 are drawn as partially crimped lines. The arrangement of the fibers creates a random entanglement.

Adhesive drops 35 are applied to some entanglement points. These are indicated by black circles.

The mixture consisting of components 33-35 is located in the air-tight pouch. The styrofoam beads 33 are uniformly distributed in the non-woven-like entanglement of the fibers 34 with the adhesive drops 35. There is air between the individual elements of the mixture. The air-tight pouch 32 is made of a material that is preferably flexible and not permeable to air. If there is air in the air-tight pouch 32 and between the styrofoam beads 33, the air-tight pouch 32 can be deformed together with the mixture.

When the air is evacuated from the air-tight pouch 32, the air-tight pouch 32 contracts and compresses the mixture contained in it. The styrofoam beads 33 and the fibers 34 come to lie close to each other and become wedged together. Owing to the high static friction that is created between the individual elements because of the reciprocal pressure, the mixture can no longer be deformed and becomes stiff. Consequently, the air-tight pouch 32 also becomes stiff. The flexible element 30 is also stiffened since the air-tight pouch 32 constitutes the stiffening means that is integrated into the flexible element 30.

As soon as air is once again let into the air-tight pouch 32, the air-tight pouch 32 and thus also the flexible element 30 can be deformed once again.

The air-tight pouch 32 shown here and filled with styrofoam beads 33 and with fibers 34 that are preferably entangled with adhesive drops 35 constitutes a stiffening means. It can be activated (evacuation of the air in the air-tight-pouch), for example, via a connection tube, and can be once again deactivated (letting air into the air-tight-pouch). It is suitable for stiffening the flexible element 30 and for returning it to a flexible state once again.

Figure 4:
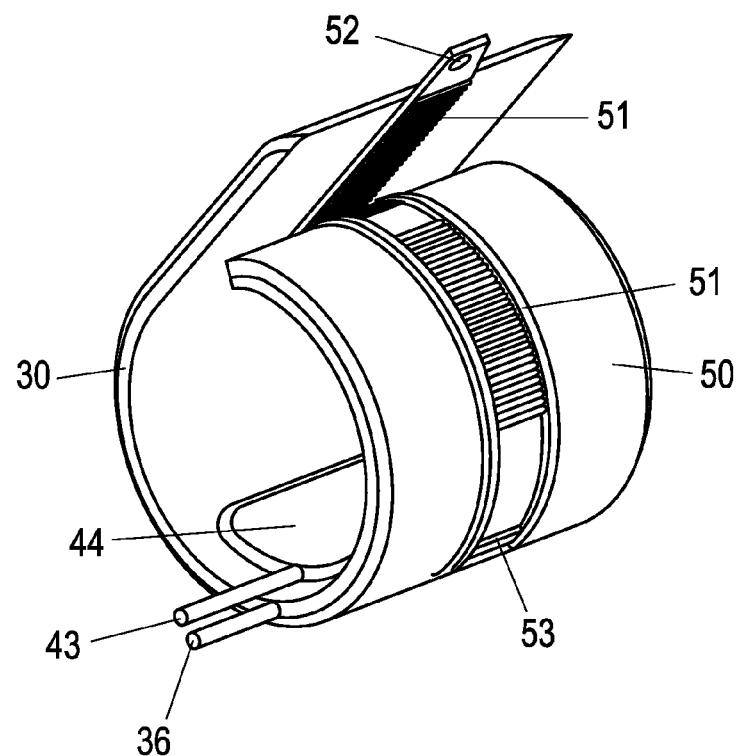
FIG. 4 a three-dimensional drawing of a preferred embodiment of the blood pressure measuring device according to the invention, with a blood-pressure cuff, gel cushion and latching strips.

FIG. 4 shows a three-dimensional drawing of a preferred embodiment of the blood pressure measuring device according to the invention, with a blood-pressure cuff, a gel cushion and latching strips.

A gel cushion 44 is attached as a pressure sensor element to the flexible element 30. A sensor cable 43 and a control line 36 for the flexible element lead out of the device.

A blood-pressure cuff is attached around the flexible element 30 as the external fixation means 50 that allows the fixation of the flexible element 30 on a body part.

Moreover an inner and outer latching strip 51 having an eyelet 53 or a tab 54 are attached to the flexible element 30 or to the external fixation means.

During the placement procedure, the combination consisting of a flexible element 30, a gel cushion 44, a blood-pressure cuff 50 and latching strips 51 is wrapped around the body part 10, so that the flexible element 30 adapts to the body part 10, and the flexible element 30 is affixed by the cuff 50 and/or the latching strips 51. Preferably, the pressure that the external fixation means 50 and/or the latching strips 51 exert on the body part can be systematically varied so that a wide array of measurements of pulsatile signals can be carried out. Due to the stiffening of the flexible element 30, the body part acquires a rigid jacket and the pressure sensor element 40 is rigidly brought into contact with the body part. This contacting is hydraulically very advantageous since energy of the pulsatile signals is not transferred to the flexible element 30 which is in its stiffened state, and thus this energy is not lost for the measurement.

Figure 5:
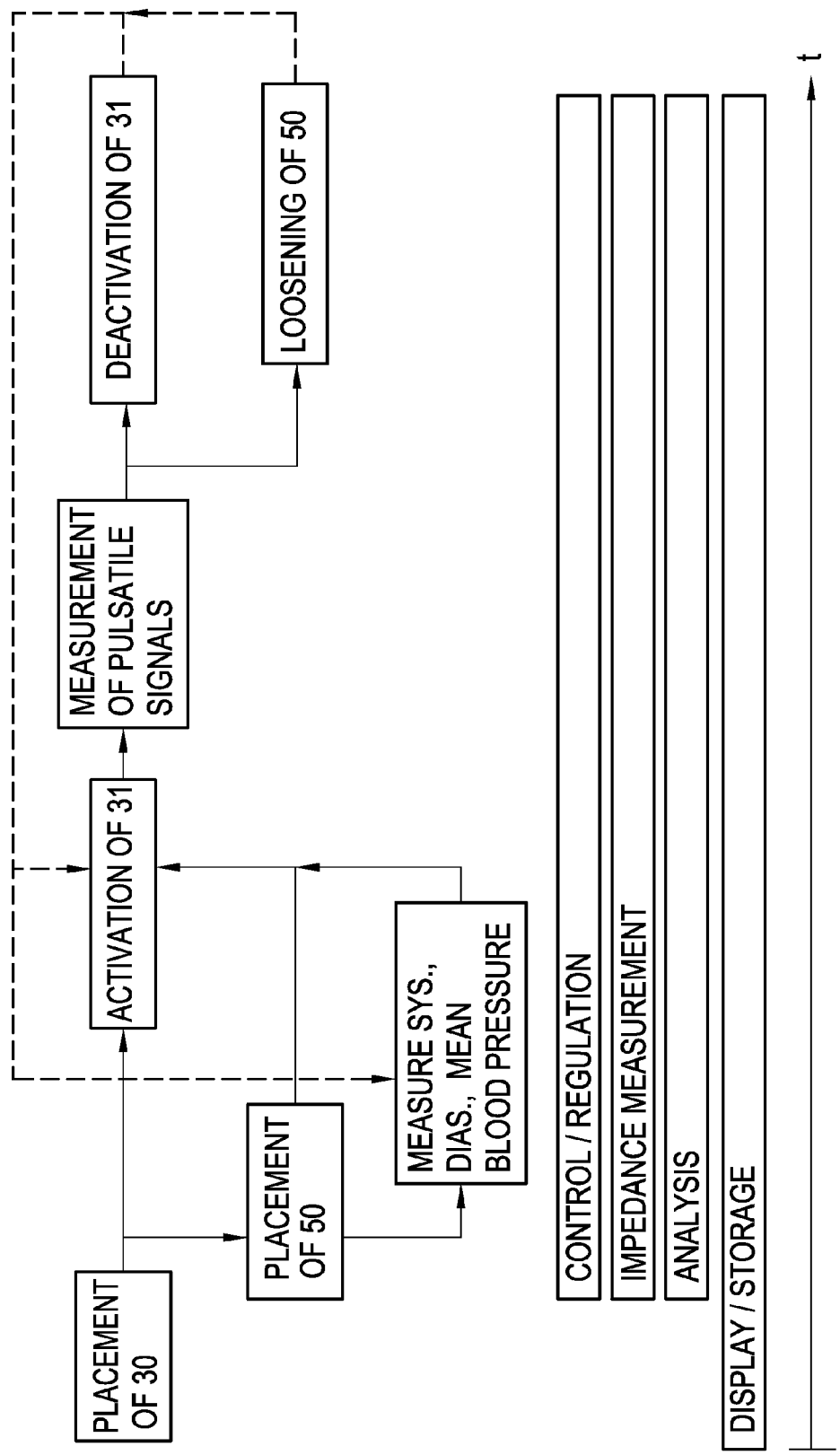
FIG. 5 a schematic flowchart of the method according to the invention.

FIG. 5 shows a schematic flowchart of the method according to the invention.

The diagram consists of labeled blocks and arrows. The blocks designate method steps. The time dependence of the method steps relative to each other is indicated by arrows whenever this is crucial. In this context, a method step that is carried out subsequently to another method step is connected by an arrow that points towards the later method step. Method steps without arrow connections do not have an obligatory time dependence with respect to other method steps. The drawn abscissa can thus be seen as a time axis. The actions indicated in blocks that have at least one shared, vertical intersecting axis can be carried out in parallel to each other in the overlapping area. If blocks are arranged precisely under each other, then the corresponding method steps can be carried out simultaneously or in any desired sequence with respect to each other. The blocks are arranged in such a way that a method sequence starts on the left-hand side and proceeds to the right-hand side. Arrows that are drawn opposite to the normal time direction do not mean a reversal of the time or a return to the past. These arrows indicate that, in preferred methods, individual steps can be executed several times, or that an entire segment of the method can be repeated. Therefore, these arrows are drawn with broken lines. If a block extends over a long section of the time axis, this means that the corresponding method step is preferably carried out during the covered period of time, starting at the point in time that is indicated by the left-hand boundary of the block. The periods of time covered by the individual method steps are not drawn to scale. The diagram does not provide any information about the actual times of execution or about the relative length of the execution times of individual method steps with respect to each other, but rather, it depicts the time sequence or order and the parallelism of the method steps according to the invention.

The method according to the invention starts with the placement of the flexible element 30 onto the body part 10 that is intended for the measurement. In this process, the flexible element 30 is put in place in such a manner that is adapts to the body part 10. This is possible thanks to the fact that the flexible element 30 remains deformable as long as the stiffening means 31 of the flexible element 30 has not been activated. Owing to the placement of the flexible element 30 which has been adapted to the body part, the pressure sensor elements 40 attached to the side of the flexible element 30 facing the body part 10 are also adapted to the body part 10. This method step is indicated by the block titled "Placement of 30".

The second step of the method according to the invention is then the activation of the stiffening means 31 or the stiffening of the flexible element 30. The flexible element 30 is then no longer be deformable. Thus, it cannot absorb or transfer any pressure fluctuations. This method step is designated by the block titled "Activation of 31".

The third step of the method according to the invention then consists of measuring the pulsatile signals over a certain period of time. The pressure sensor elements 40 attached to the flexible element 30 make hydraulically optimized contact with the body part 10 since the flexible element 30 forms a rigid outer pouch around the attached pressure sensor element 40, so that pressure fluctuations stemming from the body part 10 do not propagate into other components of the blood pressure measuring device and thus do not lose energy that then could not contribute to the signal measured by the individual pressure sensor element 40. The measuring time here encompasses, for instance, the respiratory cycles. The pressure sensor elements 40 attached to the flexible element 30 convert the pressure fluctuations into electric signals. This method step is designated by the block titled "Measurement of pulsatile signals".

In a third step, the stiffening means 31 of the flexible element 30 is deactivated once again. In the case of an airtight pouch 32 filled with styrofoam beads 33 and entangled fibers 34, the deactivation is achieved by inflating the air-tight pouch 32. This method step is designated by the block titled "Deactivation of 31".

The method block titled "Placement of 50" indicates that another preferred method entails an additional method step of placing an outer fixation means 50 around the flexible element 30. This is preferably done after the flexible element 30 has been placed on the body part 10, as shown in the diagram. The degree of the fixation of the outer fixation means is also established by the placement of the outer fixation means 50. Preferably, the degree of the fixation is established in such a way that the outer fixation means 50 exerts a pressure onto the body part 10 via the flexible element 30, said pressure being within the pulsatile range, in other words, between the systolic and the diastolic blood pressures. In this manner, the subsequent method step preferably causes the flexible element 30 to stiffen within the pulsatile range.

The method block titled "Loosening of 50" indicates that, when an outer fixation means 50 is used, it is once again loosened after the measurement. This prevents damage to the body part 10.

The method block titled "Measurement of sys., dias., mean blood pressures" indicates that, in another preferred method, the systolic and/or diastolic and/or mean blood pressures are measured. This measurement is carried out when the flexible element 30 is not yet in its stiffened state, as indicated in the diagram. Thanks to the outer fixation means 50, the pressure exerted onto the body part 10 can be systematically varied, so that an oscillatory measurement of the above-mentioned pressures can be carried out. The wide method block titled "Control/regulation" indicates that, in another preferred method, starting at the point in time when the flexible element 30 is put in place, the stiffening means 31 and/or the degree of the fixation of the outer fixation means 50 is controlled and/or regulated at every subsequent point in time or else only at certain times.

The wide method block titled "Impedance measurement" indicates that, in another preferred method, the tissue resistance is measured, starting at the point in time when the flexible element 30 is put in place. The impedance is preferably measured at one or more points in time, especially preferably alternating with the measurement of the pulsatile signals by a pressure sensor element. In a preferred method, for instance, the blood flow undergoes an impedance measurement over the course of three minutes. In this process, the blood pressure measuring device exerts essentially no pressure onto the body part. The blood can flow essentially unhindered. Then pulsatile signals are measured over the course of one minute by the pressure sensor. In this process, the outer fixation means 50 sets a pressure range that is of relevance for the measurement. The blood flow is interpolated. Subsequently, a measurement of the blood is performed once again by means of the impedance measurement, whereby the blood pressure measuring device once again exerts essentially no pressure onto the body part.

The wide method block titled "Analysis" indicates that, in another preferred method, starting at the point in time when the flexible element 30 is put in place, an analysis of the measured data is conducted. This analysis is preferably conducted at one or more points in time. For instance, the stroke volume variation (SVV) can be continuously calculated on the basis of the pulsatile blood-flow measurement (by means of impedance). The PVV, the stroke volume (SV), the heart rate (HR), the cardiac output (CO) (CO=HR×SV), $dP/dt_{max}$ as well as other parameters can all be calculated on the basis of the pressure measurement and the pulse contour.

The wide method block titled "Display/Storage" indicates that, in another preferred method, available signals and/or parameters are displayed and/or stored. This is continuously possible, starting at the point in time when they become available, but this is preferably only done starting at a certain point in time, especially preferably at several points in time.

Parts of the methods can also be executed repeatedly. For instance, after the stiffening means 31 has been deactivated and—if an external fixation means 50 is being used—preferably after the external fixation means 50 has been loosened, it is possible to continue with the stiffening of the flexible element 30 or with the oscillatory blood-pressure measurement. In this context, the backwards arrows drawn with broken lines indicate the preferred sequence paths.

The diagram in FIG. 5 illustrates how the various method steps relate to each other over the course of the method according to the invention and over the course of other methods according to the invention.

Figure 6:
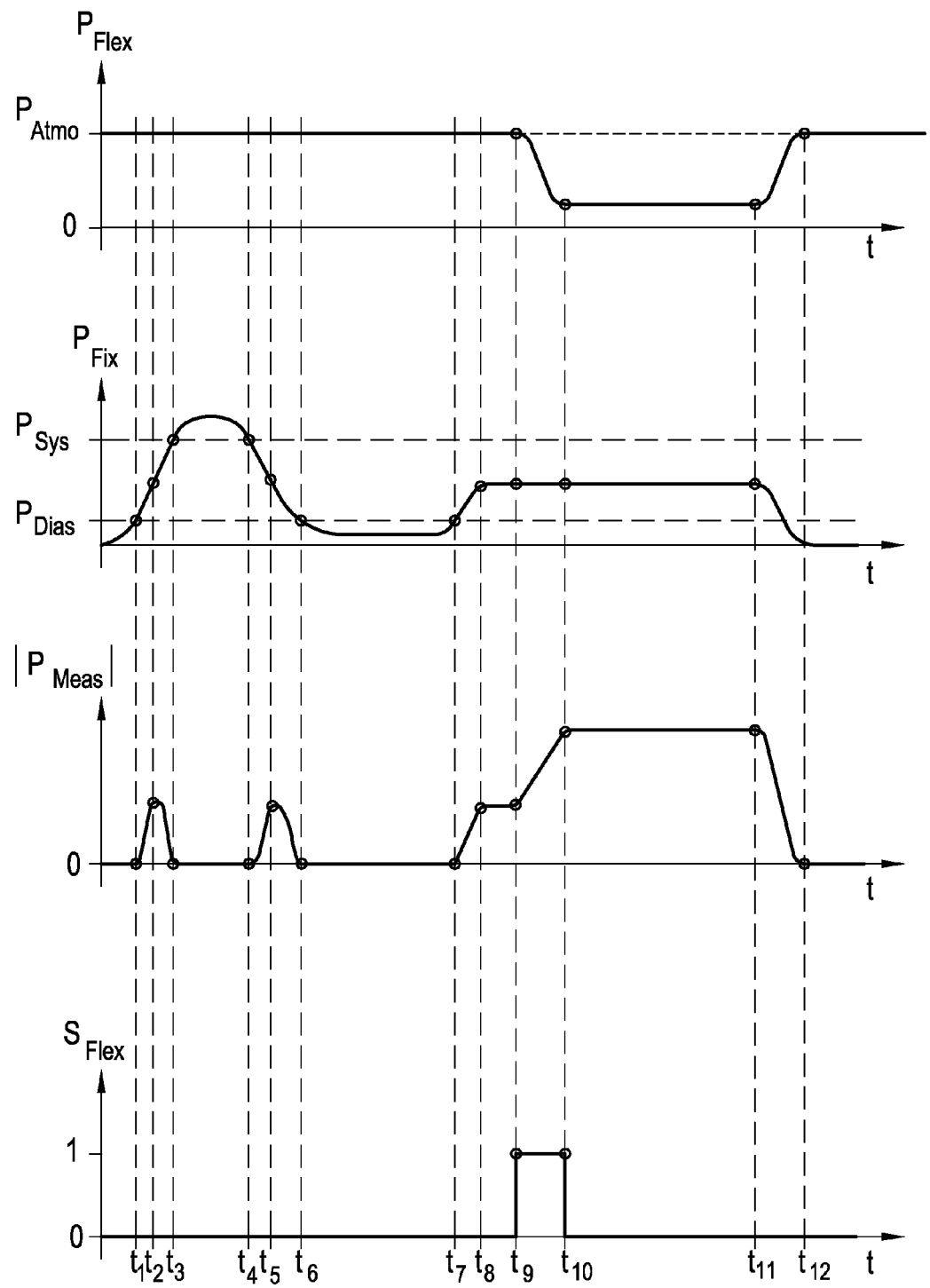
FIG. 6 the course over time of selected state parameters during the use of the blood pressure measuring device, by way of an example.

FIG. 6 shows the course over time of selected state parameters during an example of the use of the blood pressure measuring device.

Four coordinate systems have been drawn. The x-axis is the time t in each case. The uppermost axis depicts the course of the air pressure $P_{Flex}$ in the flexible element 30 relative to the atmospheric ambient pressure $P_{Atmo}$. The second diagram from the top depicts the pressure $P_{Fix}$ of the outer fixation means 50 exerted onto the flexible element 30, and thus onto the body part 10, relative to the values of the systolic and diastolic pressures $P_{Sys}$ and $P_{Dias}$, respectively. The third axis system from the top depicts the course of $|P_{Meas}|$. This is the mean value of the amplitude of the pressure measured by the pressure sensor element 40 over the course of at least one respiratory breathing cycle. The lowermost diagram depicts the course of a control signal $S_{Flex}$ for activating the stiffening means 31. A pump, for example, is controlled by means of this signal. The value 0 stands for "OFF" while the value 1 stands for "ON".

In the beginning, the systolic, diastolic and mean blood pressures are ascertained. For this purpose, $P_{Fix}$ is increased. Starting at the point in time $t_1$, pulsatile signals are measured by the pressure sensor element so that $|P_{Meas}|$ also rises. At a point in time $t_2$, at which $P_{Fix}$ traverses the value of the mean blood pressure, $|P_{Meas}|$ exhibits a local maximum. At the point in time $t_3$, $P_{Fix}$ exceeds the value of the systolic blood pressure and $|P_{Meas}|$, is once again 0. If $P_{Fix}$ is lowered further, pulsatile signals occur and thus $|P_{Meas}|>0$ between the points in time $t_4$ and $t_6$, with a local maximum of $|P_{Meas}|$ at $t_5$. The systolic, diastolic and mean blood pressures can be ascertained on the basis of this measuring sequence. Subsequently, $P_{Fix}$ is increased from the point in time $t_7$ to the point in time $t_8$, so that, starting at $t_8$, the $P_{Fix}$ is set at a value close to the mean blood pressure. $|P_{Meas}|$ then assumes a value that is equal to or smaller than the value of the local maxima already reached at the points in time $t_2$ and $t_5$. At the point in time $t_9$, the control signal $S_{Flex}$ is increased from 0 to 1, that is to say, the flexible element 30 is stiffened. The transition to the stiffened state lasts from $t_9$ to $t_{10}$. During this time, air is evacuated from the flexible element. The pressure in the flexible element $P_{Flex}$ drops to below the ambient $P_{Atmo}$. As the evacuation progresses, the hydraulic contact of the pressure sensor element 40 with the body part 10 is improved so that the signal quality rises and thus $|P_{Meas}|$ also rises above a value of the previously reached local maxima, in other words, the signal-to-noise ratio is improved. At the point in time $t_{10}$, $P_{Flex}$ has reached a predetermined low value and the pump is switched off, that is to say, $S_{Flex}$ is set from 1 to 0, and the flexible element is sealed off by a valve. Between $t_{10}$ and $t_{11}$, the pulsatile signals are then measured with a very good signal quality. At the point in time $t_{11}$, the outer fixation means 50 is loosened once again and the flexible element 30 is once again inflated by opening the appropriate valve, so that the values of $P_{Flex}$, $P_{Fix}$ and $|P_{Meas}|$ return to their initial state by the point in time $t_{12}$.

Figure 7:
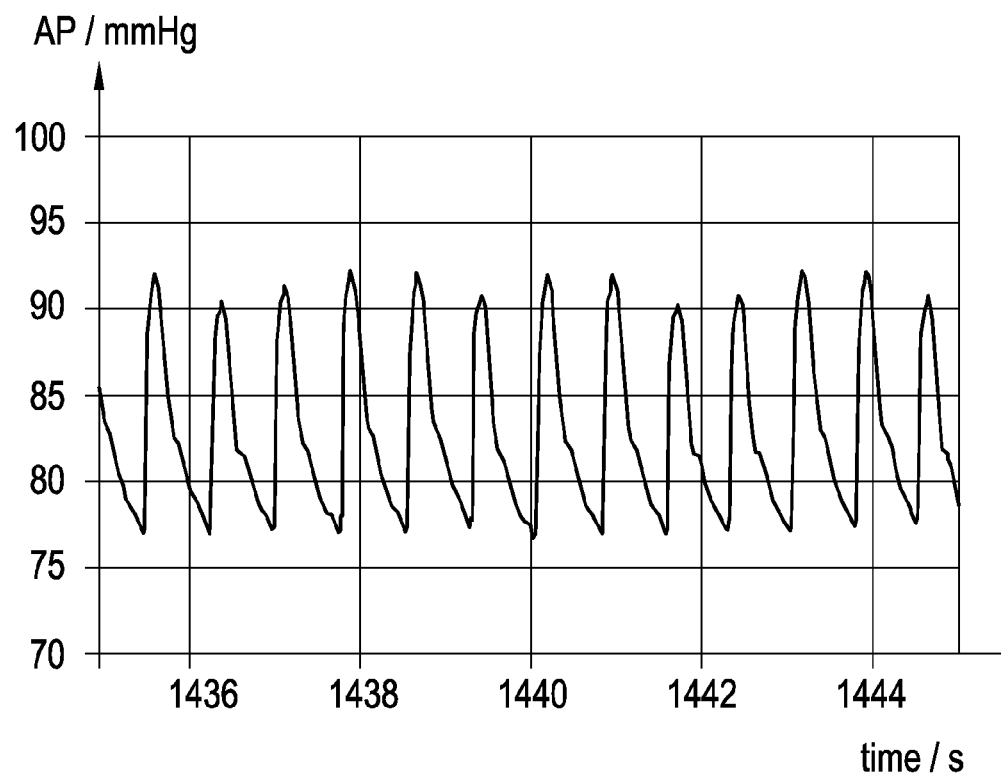
FIG. 7 the course over time of the pressure curve measured by a pressure sensor in the version of the blood pressure measuring device with an external fixation means that does not completely overlap the flexible element at all of the ends.
Figure 7:
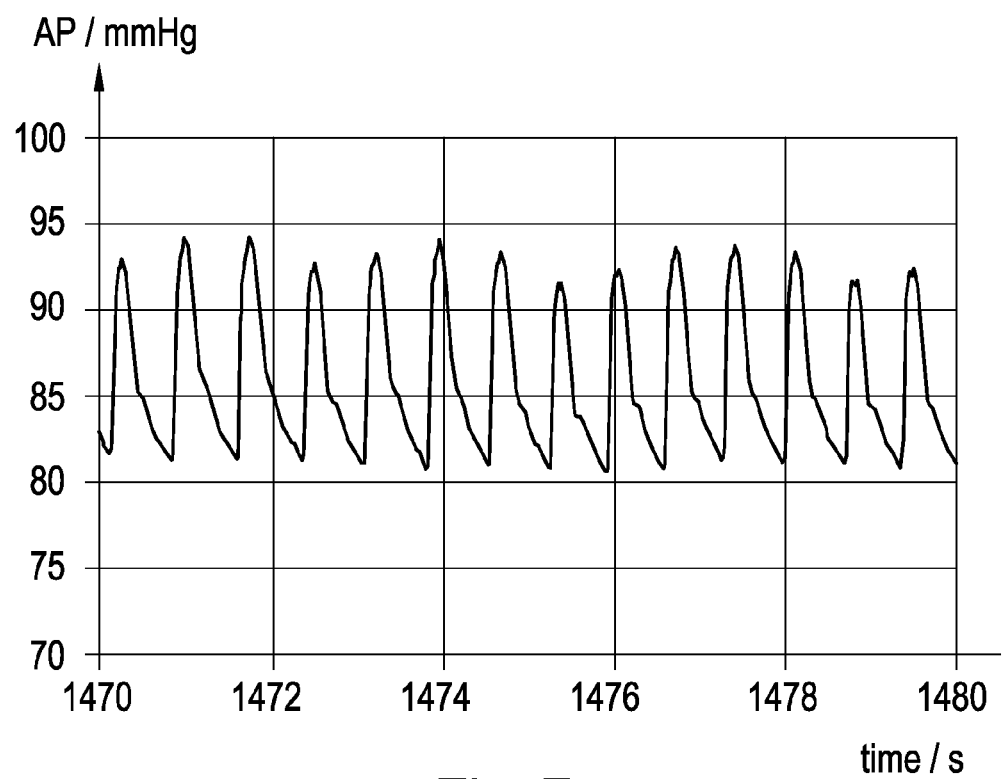

FIG. 7 shows the course over time of the pressure curve measured by a pressure sensor in the version of the blood pressure measuring device with an external fixation means that does not completely overlap the flexible element at all of the ends.

In this embodiment, the flexible element consists of an air-tight pouch that can be evacuated and that is filled with a stack of paper made up of 40 sheets with a paper weight of 80 g/m². This flexible element is in a conventional blood-pressure cuff and is wrapped around the upper arm, along with the cuff. The blood-pressure cuff, however, does not overlap the flexible element in the lengthwise direction of the arm, but rather, the flexible element protrudes out of the blood-pressure cuff. A YoYo pressure sensor (trademark of the Up-Med company) is located as the pressure sensor element between the flexible element and the skin.

This figure now shows two graphs. The lower graph describes the pressure course measured with an electronic high-fidelity pressure sensor (in this case, a YoYo pressure sensor—trademark of the Up-Med company) with an inflated air-tight pouch, while the upper graph describes the case with an evacuated air-tight pouch. One can clearly see the course of the pulse beat. The bottom curve (inflated pouch) exhibits disjunct peaks and interference noise in the signal). The upper signal curve (evacuated pouch) no longer exhibits these interferences as clearly. Generally speaking, the signal of both graphs, however, is a bit blurry since the secondary peaks are not clearly recognizable.

Figure 8:
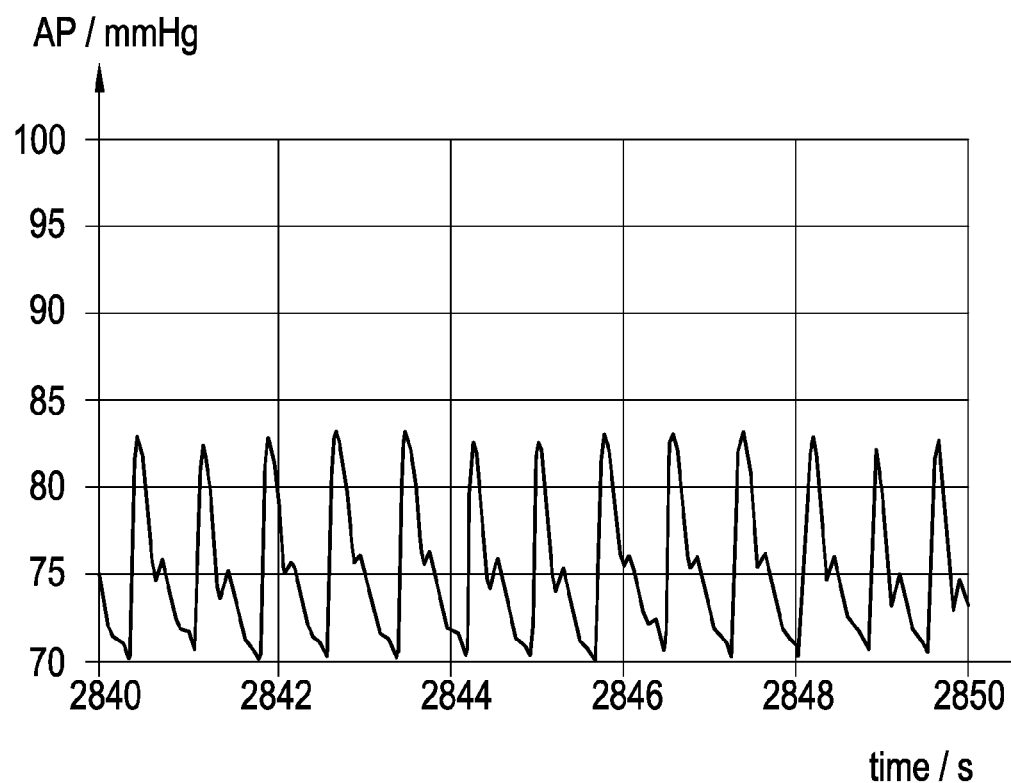
FIG. 8 the course over time of the pressure curve measured by a pressure sensor in the version of the blood pressure measuring device with an external fixation means that completely overlaps the flexible element at all of the ends.
Figure 8:
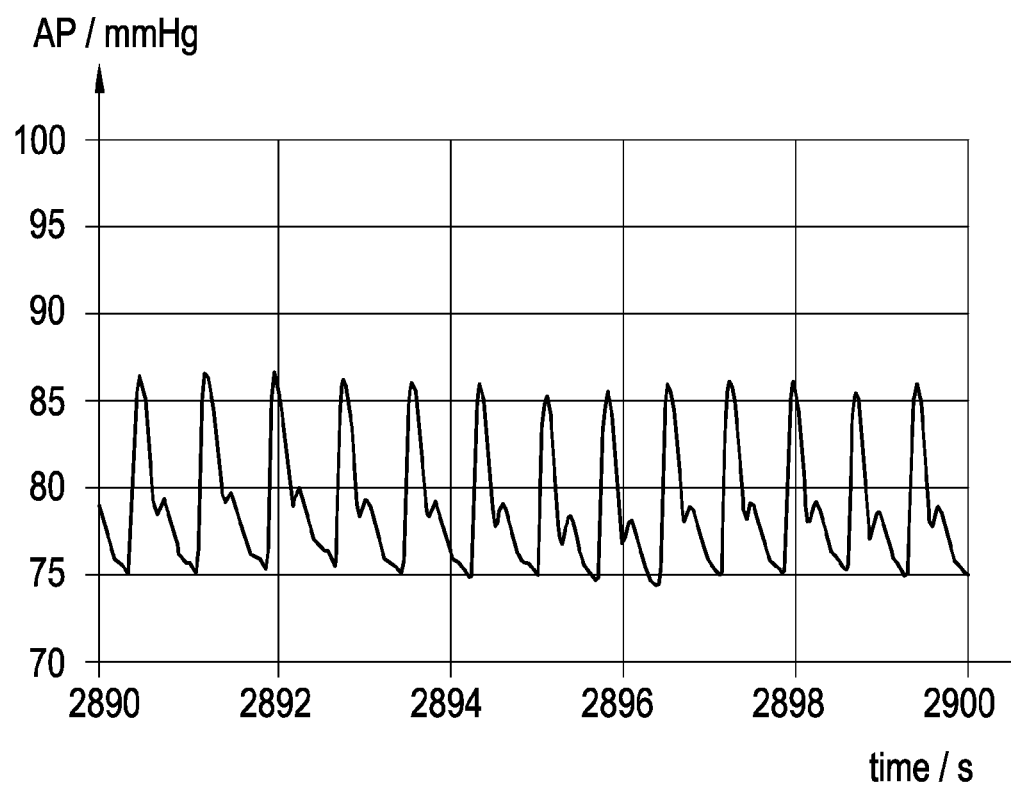

FIG. 8 shows the course over time of the pressure curve measured by a pressure sensor in the version of the blood pressure measuring device with an external fixation means that completely overlaps the flexible element at all of the ends.

The difference between this embodiment of the blood pressure measuring device and that of the blood pressure measuring device shown in the previous figure is that now the conventional blood-pressure cuff completely covers the stack of paper located in the air-tight pouch.

Here as well, one can see two graphs showing the measured pressure signals in the case of an evacuated pouch (top) and an inflated pouch (bottom). It is noticeable that signals of very high quality are measured with this embodiment. The difference between the evacuated air-tight pouch and the inflated air-tight pouch is no longer very large. However, the secondary peaks can be clearly seen in the upper graph (evacuated pouch). The signal quality, which is already very high in the non-evacuated pouch, is related to the pressure-resistance of the stack of papers, which is already very high in the non-evacuated state.

LIST OF REFERENCE NUMERALS 10 body part
20 blood pressure measuring device
30 flexible element
31 stiffening means
311 sheet of paper
32 air-tight pouch
33 styrofoam beads
331 incompressible elements
34 fibers
341 cotton/wool fibers
342 fabric
343 plastic net
35 adhesive drops
36 control line for the flexible element
40 pressure sensor element
41 pressure sensor
42 electrodes
43 sensor cable
44 gel cushion
50 outer fixation means
51 latching strips
52 control line for the outer fixation means
53 eyelet
54 tab
60 control device

What is claimed is:

1. A blood pressure measuring device comprising:
    a single air-tight pouch having a connection tube, the air-tight pouch functioning as a flexible element configured to at least partially surround a body part;
    a stiffening element disposed in the air-tight pouch and configured to stiffen the flexible element by evacuating air contained in the air-tight pouch;
    at least one pressure sensor element having a sensor cable attached to an inside surface of the flexible element that is to be pressed against the body part such that, during use, the at least one pressure sensor element will contact the body part; and
    a control device configured to control the stiffening element by controlling the level of vacuum in the air-tight pouch.

2. The blood pressure measuring device as recited in claim 1, wherein the at least one pressure sensor element is a pressure sensor embedded in a gel cushion.

3. The blood pressure measuring device as recited in claim 1, further comprising at least one additional sensor.

4. The blood pressure measuring device as recited in claim 1, further comprising an external fixation device arrangeable at least partially around the flexible element.

5. The blood pressure measuring device as recited in claim 1, wherein the at least one pressure sensor element is one of a sensor or a combination of sensors selected from the group of sensors consisting of an electrode for impedance measurement, an electrode for potential measurement, a photoelectric sensor, a capacitive sensor and an acceleration sensor.

6. The blood pressure measuring device as recited in claim 1, wherein the air-tight pouch includes essentially incompressible elements having a volume in a vacuum configured to change less than 50% in comparison to a volume at atmospheric pressure.

7. The blood pressure measuring device as recited in claim 1, wherein the air-tight pouch has entangled fibers.

8. The blood pressure measuring device as recited in claim 1, wherein the air-tight pouch includes styrofoam beads.

9. The blood pressure measuring device as recited in claim 1, wherein the flexible element includes at least one latching strap.

10. The blood pressure measuring device as recited in claim 1, further comprising an analysis device configured to at least one of analyze, display and store measured data.

11. A method for measuring the blood pressure of a living being, the method comprising:
using a blood pressure measuring device comprising:
a single air-tight pouch having a connection tube, the air-tight pouch functioning as a flexible element configured to at least partially surround a body part;
a stiffening element disposed in the air-tight pouch and configured to stiffen the flexible element by evacuating air contained in the air-tight pouch;
at least one pressure sensor element having a sensor cable attached to an inside surface of the flexible element that is to be pressed against the body part such that, during use, the at least one pressure sensor element will contact the body part; and
a control device configured to control the stiffening element by controlling the level of vacuum in the air-tight pouch,
placing the flexible element with the blood pressure sensor element onto a body part to be measured such that the flexible element assumes a shape adapted to the body part;
changing the flexible element to the stiffened state in the assumed shape;
measuring the pressure signal over a certain period of time while the flexible element is in the stiffened state; and
returning the flexible element to a non-stiffened state.

12. The method as recited in claim 11, wherein the flexible element includes an external fixation device.

13. The method as recited in claim 12, wherein the changing the flexible element to the stiffened state includes stiffening the flexible element to make it incompressible.

14. The method as recited in claim 11, wherein the changing is performed by evacuating air contained in the flexible element.

15. The method as recited in claim 11, wherein the changing is performed by filling the flexible element with compressed air.

16. The method as recited in claim 12, wherein the external fixation device is a blood-pressure cuff.

17. The method as recited in claim 14, wherein the external fixation device is a blood-pressure cuff, and further comprising pumping the evacuated air into the external blood-pressure cuff.

18. The method as recited in claim 16, further comprising varying a pressure in the blood-pressure cuff so as to measure a systolic, a diastolic and a mean blood pressure.

19. The method as recited in claim 11, wherein the changing is performed when an arterial pressure is between a mean and a diastolic blood pressure.

20. The method as recited in claim 11, further comprising controlling at least one of the changing, a degree of fixation and an acquiring of a sensor value using a control device.

21. The method as recited in claim 11, further comprising measuring an electric impedance of the body part.

22. The method as recited in claim 18, further comprising determining a shape of an arterial curve in the body part based on at least one of the measured systolic, diastolic and mean blood pressure.

23. The method as recited in claim 11, further comprising changing the flexible element to the non-stiffened state after a predetermined time period.

24. The method as recited in claim 12, further comprising loosening the external fixation device after a predetermined time period.

* * * * *